(12) United States Patent
Kawase et al.

(10) Patent No.: US 7,955,494 B2
(45) Date of Patent: Jun. 7, 2011

(54) GAS SENSOR CONTROL APPARATUS

(75) Inventors: Tomoo Kawase, Aichi-ken (JP); Eiichi Kurokawa, Okazaki (JP); Toshiyuki Suzuki, Handa (JP); Takahito Masuko, Anjo (JP)

(73) Assignee: Denso Corporation, Kariya (JP)

( * ) Notice: Subject to any disclaimer, the term of this patent is extended or adjusted under 35 U.S.C. 154(b) by 315 days.

(21) Appl. No.: 12/212,121

(22) Filed: Sep. 17, 2008

(65) Prior Publication Data
US 2009/0084677 A1  Apr. 2, 2009

(30) Foreign Application Priority Data

Sep. 27, 2007  (JP) ................................ 2007-252622

(51) Int. Cl.
*G01N 27/417* (2006.01)
(52) U.S. Cl. ........ 205/785; 204/406; 204/425; 73/23.32
(58) Field of Classification Search .................. 204/406, 204/425, 427; 205/785; 73/23.31, 23.32
See application file for complete search history.

(56) References Cited

U.S. PATENT DOCUMENTS

| | | | | |
|---|---|---|---|---|
| 4,591,421 A | * | 5/1986 | Yamada et al. | 204/406 |
| 5,758,310 A | * | 5/1998 | Kato | 701/109 |
| 6,084,418 A | * | 7/2000 | Takami et al. | 324/717 |
| 2005/0029098 A1 | | 2/2005 | Aoki et al. | |

FOREIGN PATENT DOCUMENTS

| | | |
|---|---|---|
| JP | 05-040105 | 2/1993 |
| JP | 2002-005882 | 1/2002 |
| JP | 2005-055279 | 3/2005 |

OTHER PUBLICATIONS

Japanese Office Action dated Nov. 17, 2009, issued in corresponding Japanese Application No. 2007-252622, with English translation.

* cited by examiner

*Primary Examiner* — Kaj K Olsen
(74) *Attorney, Agent, or Firm* — Nixon & Vanderhye P.C.

(57) ABSTRACT

The gas sensor control apparatus is for controlling a gas sensor including a sensor element having a solid electrolyte layer, and first and second electrodes located on opposite sides of the solid electrolyte layer, the first electrode serving as a gas detecting electrode, the second electrode serving as a reference electrode, the sensor element generating, as a sensor output, a current flowing between the first and second electrodes having a value depending on concentration of a specific gas component contained in a gas under measurement. The gas sensor control apparatus includes a determination function of determining whether or not it is time for the gas sensor to start operation, and a control function of forcibly supplying oxygen from a side of the second electrode to a side of the first electrode on a temporary basis when a determination result of the first function becomes affirmative.

24 Claims, 22 Drawing Sheets

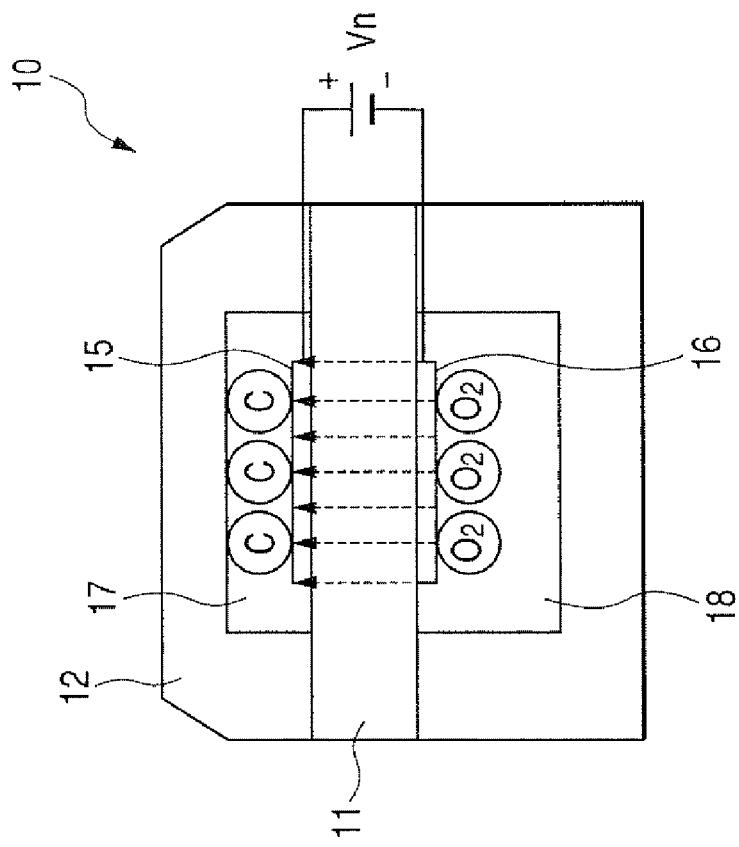
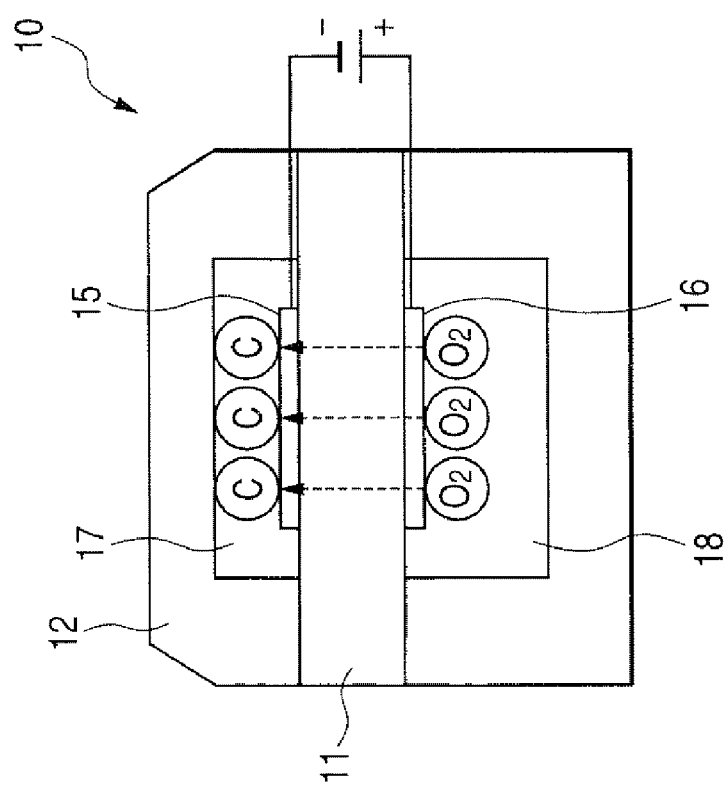

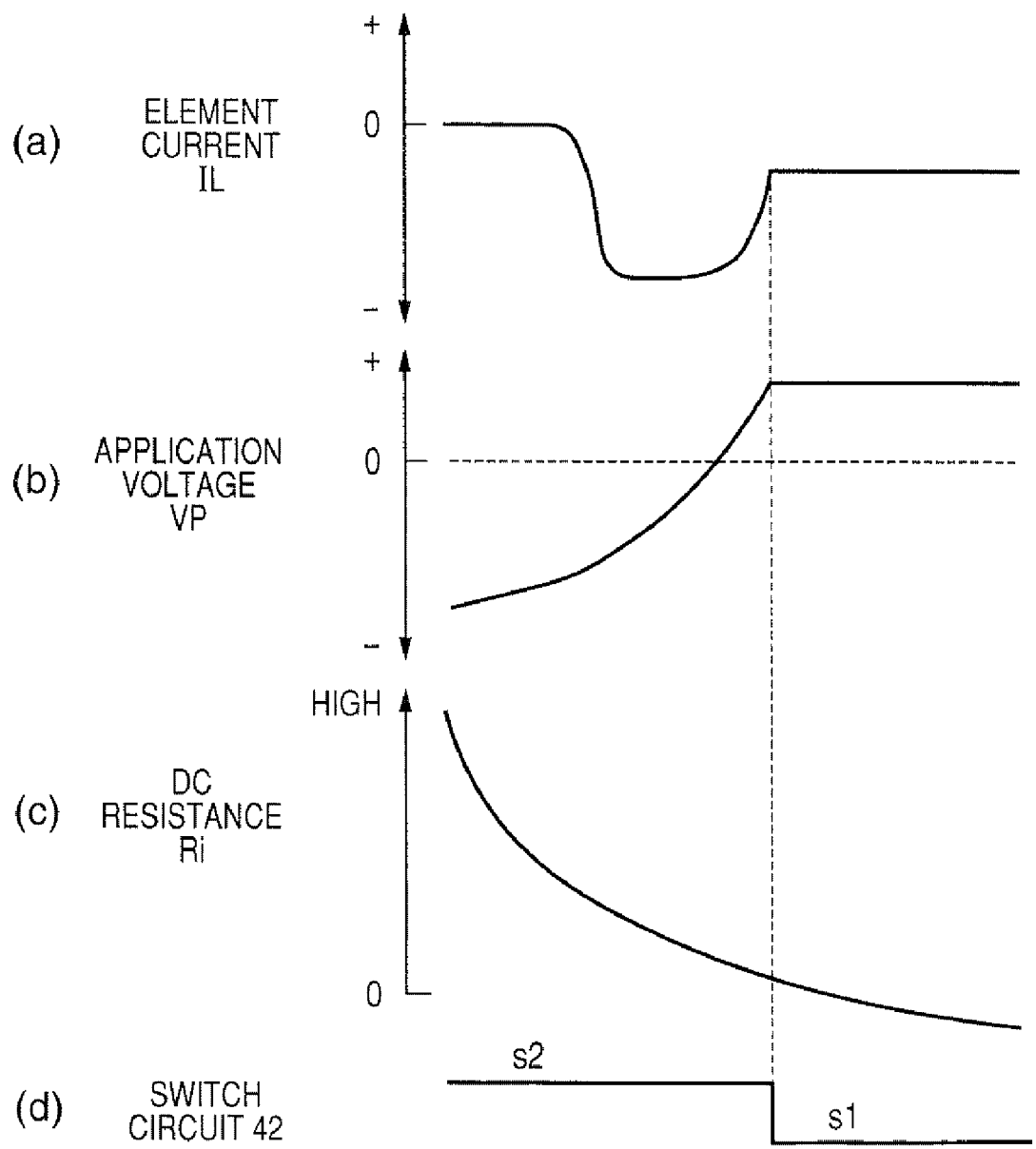

GAS SENSOR CONTROL APPARATUS

CROSS-REFERENCE TO RELATED APPLICATION

This application is related to Japanese Patent Application No. 2007-252622 filed on Sep. 27, 2007, the contents of which are hereby incorporated by reference.

BACKGROUND OF THE INVENTION

1. Field of the Invention

The present invention relates to a gas sensor control apparatus.

2. Description of Related Art

Limiting-current type oxygen concentration sensors are in practical use in vehicle engines to measure oxygen concentration in exhaust gas. This type of oxygen concentration sensor includes a sensor element constituted of a solid electrolyte layer made of, for example, zirconia, and a pair of electrodes located on the opposite sides of the solid electrolyte layer. When a voltage is applied across the electrodes, the sensor element outputs a current signal having a value depending on oxygen concentration in exhaust gas.

The sensor element has to be heated to a predetermined temperature range (about 700-800 degrees C.), so that it is put in an active state in which the current signal can be outputted accurately, enabling detection of oxygen concentration or an A/F (air-fuel ratio). Generally, the sensor element is provided with an electrical heater. When a vehicle engine is started, the heater is energized to put the sensor element in the active state, and thereafter, the heater is energized as necessary to keep the sensor element in the active state.

To determine whether the sensor element has entered the active state, an activation judgment is performed. As one way of making such an activation judgment, it is known to measure an element impedance of the sensor element, and use the measured element impedance as a judgment parameter. For details, refer to Japanese patent Application Laid-open No. 2002-5882, for example. There is a certain correlation between the temperature of the sensor element and the element impedance. As the temperature of the sensor element increases, the element impedance decreases. Accordingly, it is possible to judge that the sensor element has entered the active state by detecting that the element impedance has fallen below a predetermined threshold (several tens of ohms, for example).

On the other hand, recently, with the aim of starting an air-fuel ratio feedback control as soon as a vehicle engine is started, attempts have been made to monitor a sensor output, and make a judgment that the sensor has entered the active state when the sensor output has converged within a predetermined normal range. However, the inventors of the present application have found that it takes a long time for the sensor output to converge within a predetermined normal range from the start of a vehicle engine, because moisture or organic matter adheres to the sensor element while the engine is stopped. This delays making a judgment that the sensor element has entered the active state.

SUMMARY OF THE INVENTION

The present invention provides a gas sensor control apparatus for controlling a gas sensor including a sensor element having a solid electrolyte layer, and first and second electrodes located on opposite sides of the solid electrolyte layer, the first electrode serving as a gas detecting electrode, the second electrode serving as a reference electrode, the sensor element generating, as a sensor output, a current flowing between the first and second electrodes having a value depending on concentration of a specific gas component contained in a gas under measurement, the gas sensor control apparatus comprising:

a determination function of determining whether or not it is time for the gas sensor to start operation; and a control function of forcibly supplying oxygen from a side of the second electrode to a side of the first electrode on a temporary basis when a determination result of the first function becomes affirmative.

According to the present invention, it is possible to provide a gas sensor control apparatus capable of quickly bringing a sensor output of a gas sensor to a normal level, to thereby make a determination at an early stage that the gas sensor has entered an active state.

Other advantages and features of the invention will become apparent from the following description including the drawings and claims.

BRIEF DESCRIPTION OF THE DRAWINGS

In the accompanying drawings:

FIGS. 5A and 5B are diagrams for explaining a voltage application control performed by the gas sensor control apparatus shown in FIG. 1;

FIG. 12 is a time chart showing variations with time of an element current etc., when the negative voltage control is performed on the A/F sensor by the gas sensor control apparatus shown in FIG. 10;

PREFERRED EMBODIMENTS OF THE INVENTION

First Embodiment

Figure 1:
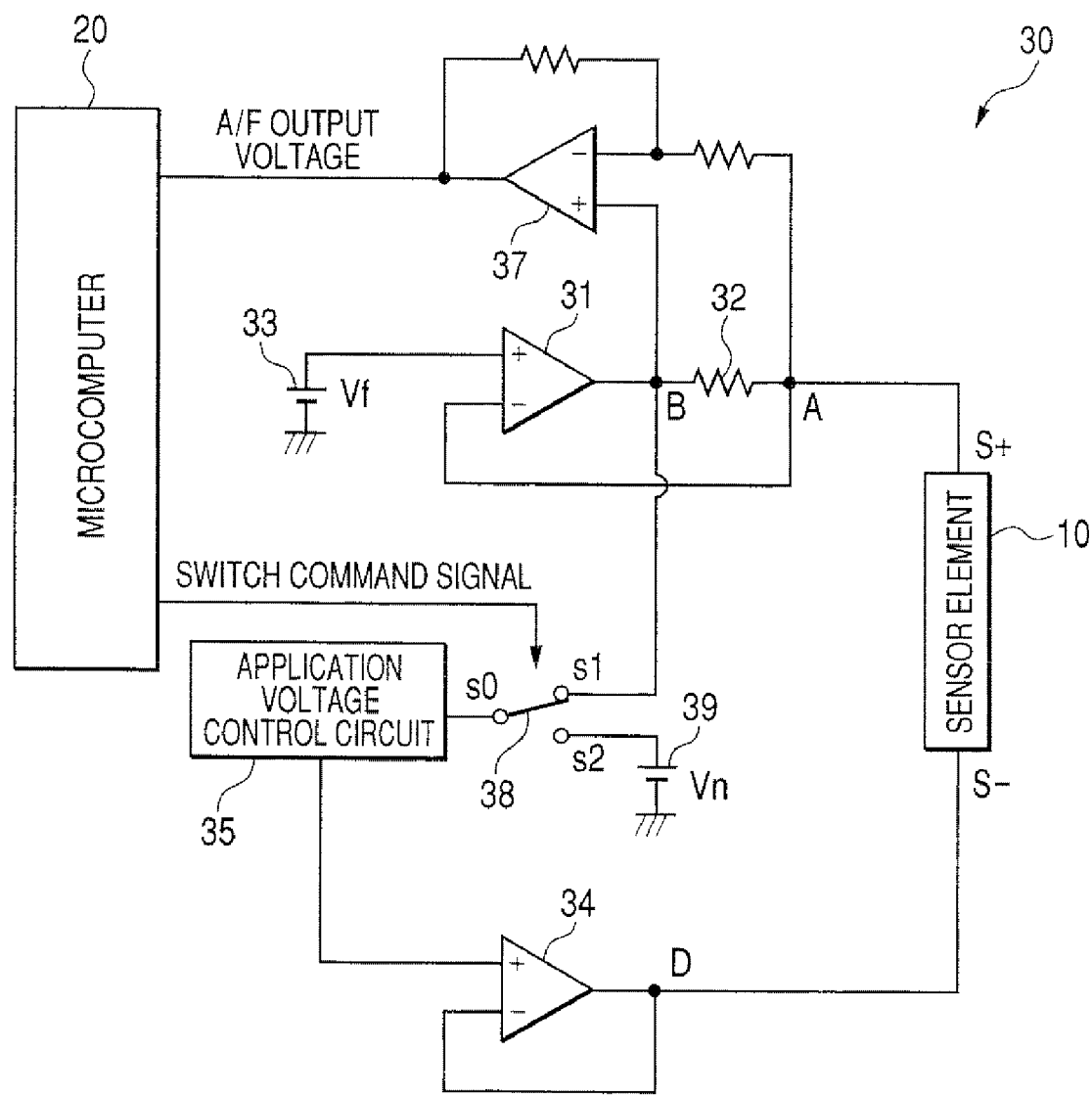
FIG. 1 is a circuit diagram of a gas sensor control apparatus according to a first embodiment of the invention.

In the below-described embodiments, the same or corresponding components are represented by the same reference numerals or characters.

Figure 2:
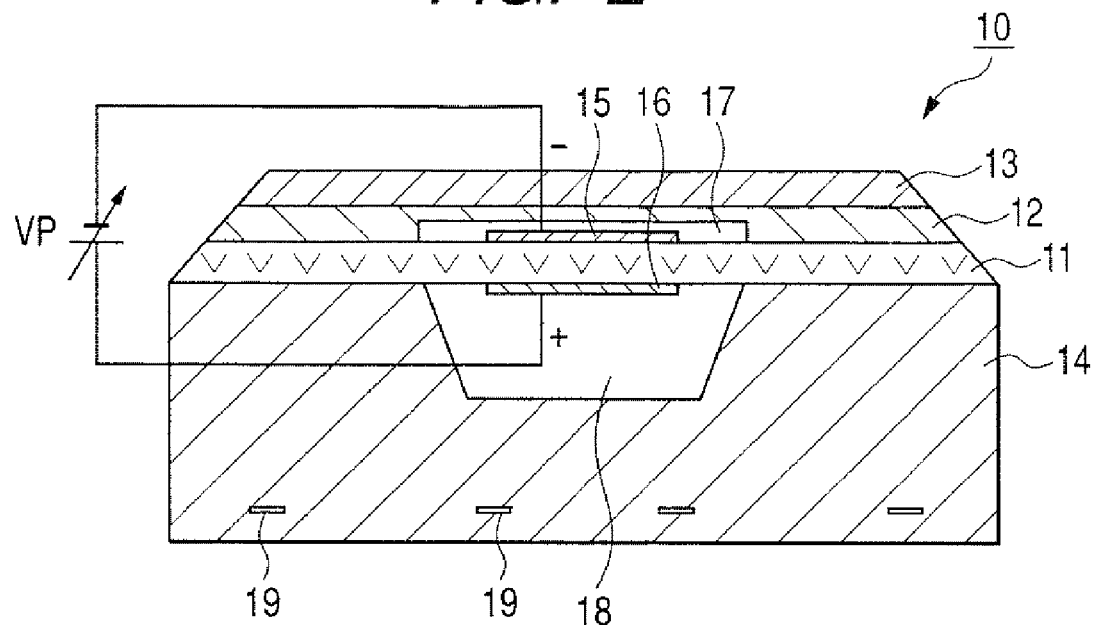
FIG. 2 is a cross-sectional view of a sensor element of an A/F sensor controlled by the gas sensor control apparatus shown in FIG. 1.

Before describing a gas sensor control apparatus according to a first embodiment of the invention, a structure of an A/F sensor (air-fuel ratio sensor) as a control object of the gas sensor control apparatus is explained with reference to FIG. 2. The A/F sensor includes a lamination-type sensor element 10. FIG. 2 is a diagram showing a cross-sectional structure of the sensor element 10. The sensor element 10, which has a slender shape extending in the direction perpendicular to FIG. 2, is housed in a housing or an element cover. In this embodiment, the A/F sensor is mounted on an exhaust pipe to measure an air-fuel ratio of an exhaust gas flowing through the exhaust pipe.

The sensor element 10 includes a solid electrolyte layer 11, a diffusion resistance layer 12, a shielding layer 13, and an insulating layer 14 laminated in succession. Although not shown in the drawing, the sensor element 10 is provided with a protection layer at its periphery. The solid electrolyte layer 11, which has a rectangular plate shape, is a sheet made of partially stabilized zirconia. A pair of electrodes 15 and 16 are located on the opposite sides of the solid electrolyte layer 11. The diffusion resistance layer 12 is made of a porous sheet which allows the exhaust gas to be introduced into the electrode 15. The shielding layer 13 is a dense layer impermeable to the exhaust gas. The diffusion resistance layer 12 is formed with an exhaust gas chamber 17 surrounding the electrode 15.

The diffusion resistance layer 12 and the shielding layer 13 are both made by forming ceramic such as alumina, spinel or zirconia in a shape of sheet. However, they have different gas permeabilities due to differences in their average porosity diameters and porosity ratios.

The insulating layer 14, which is made of high heat-conductive ceramic such as alumina, is formed with an atmosphere duct 18 at a portion facing the electrode 16. The insulating layer 14 includes a heater 19 embedded therein. The heater 19 generates heat when supplied with an electric current from a battery source to heat the whole of the sensor element 10.

The electrode 15 located on the side of the exhaust gas chamber 17 to serve as a gas detecting electrode may be referred to as an "exhaust-gas-side electrode 15" hereinafter. The electrode 16 located on the side of the atmosphere duct 18 to serve as a reference electrode may be referred to as an "atmosphere-side electrode 16" hereinafter.

The exhaust gas around the sensor element 10 enters inside the sensor element 10 from a side portion of the diffusion layer 12, and then flows into the exhaust gas chamber 17 through the diffusion layer 12 to reach the exhaust-gas-side electrode 15. When the exhaust gas is lean, oxygen is removed from the exhaust gas at the exhaust-gas-side electrode 15, and discharged to the atmosphere duct 18 through the solid electrolyte layer 11 and the atmosphere-side electrode 16. When the exhaust gas is rich, oxygen is removed from the air in the atmosphere duct 18 at the atmosphere-side electrode 16, and discharged to the exhaust gas chamber 17 through the solid electrolyte layer 11 and the exhaust-gas-side electrode 15.

In this embodiment, the exhaust-gas-side electrode 15 is defined as a negative electrode, and the atmosphere-side electrode 16 is defined as a positive terminal. Further, in this embodiment, when an application voltage VP applied between the electrodes 15, 16 takes a positive value, the voltage of the exhaust-gas-side electrode 15 is regarded as negative (−), and the voltage of the atmosphere-side electrode 16 is regarded as positive (+), as shown in FIG. 2. Conversely, when the application voltage VP applied between the electrodes 15, 16 takes a negative value, the voltage of the exhaust-gas-side electrode 15 is regarded as positive (+), and the voltage of the atmosphere-side electrode 16 is regarded as negative (−).

Figure 3:
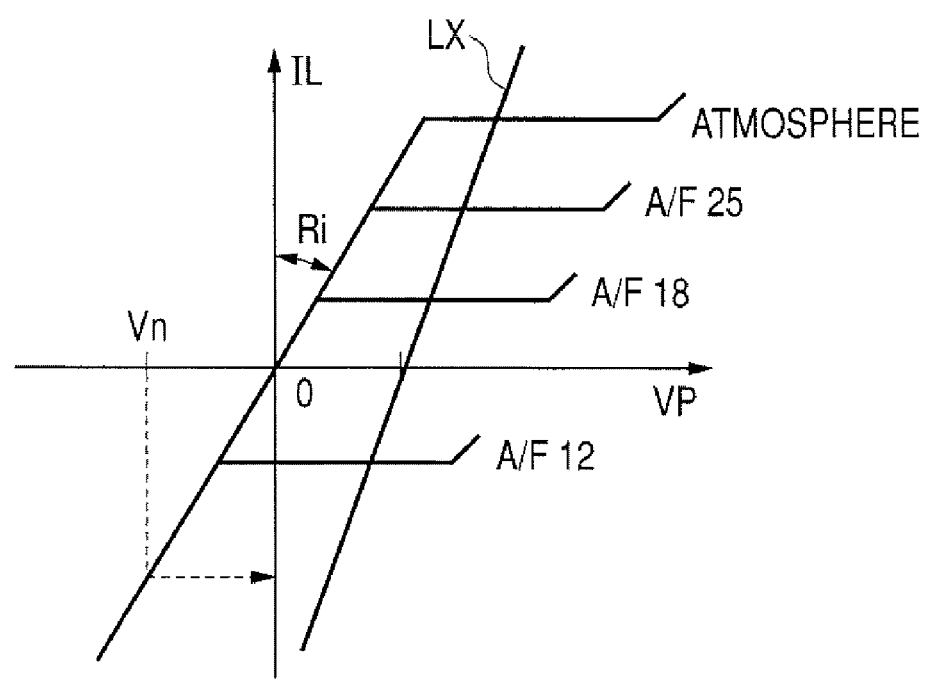
FIG. 3 is a graph showing an output characteristic (V-I characteristic) of the A/F sensor.

FIG. 3 is a graph showing an output characteristic (V-I characteristic) of the sensor element 10. In the graph of FIG. 3, a portion shown by straight lines (a flat portion) parallel to the horizontal axis (VP axis) is called a limiting current region where the element current IL is defined as a limiting current. In this region, there is a correlation between the element current IL and the air-fuel ratio. More specifically, in this region, as the air-fuel ratio moves to the lean side, the element current IL decreases.

In this graph, a slope region on the lower voltage side than the limiting current region is called a resistance-dominant region. The degree of slope of this resistance-dominant region depends on a DC resistance Ri of the sensor element 10. When the temperature of the sensor element (may be referred to as "element temperature" hereinafter) is low, and accordingly the DC resistance Ri of the sensor element is large, the slope of the slope region is small, while on the other hand, when the element temperature is high, and accordingly the DC resistance Ri is small, the slope of the slope region is large. The reference letters LX in this graph denote an application-voltage characteristic line (an application-voltage map set in a first-order line). The slope of this application-voltage characteristic line is roughly the same as the slope of the resistance-dominant region.

Next, the electrical structure of a gas sensor control apparatus according to a first embodiment of the invention is explained with reference to FIG. 1.

As shown in FIG. 1, the gas sensor control apparatus is constituted by a microcomputer 20 and a sensor control circuit 30. The microcomputer 20, which includes a CPU, various memories, an A/D converter, etc., receives, from the sensor control circuit 30, an A/F output voltage corresponding to the element current to calculate an A/F value representing an A/D-converted value of the A/F output voltage. This A/D-converted value is successively outputted to a not-shown engine ECU.

The sensor control circuit includes an amplifier circuit 37, operational amplifiers 31 and 34, an application voltage control circuit 35, a switch circuit 38, a current measuring resistor 32, a reference voltage source 33, and a negative voltage source 39. The sensor element 10 is connected at its positive terminal (S+ terminal) to the reference voltage source 33 through the operational amplifier 31 and the current measuring resistor 32, and also connected at its negative terminal (S– terminal) to the application voltage control circuit 35 through the operational amplifier 34. The voltage of a node point A on the one end side of the current measuring resistor 32 is kept at the same voltage as a reference voltage Vf (2.2 V, for example) of the reference voltage source 33. The element current flows through the current measuring resistor 32, and accordingly, the voltage of a node point B on the other end side of the current measuring resistor 32 varies depending on the value of the element current. When the exhaust gas is lean, since a current flows from the S+ terminal to the S– terminal of the sensor element 10, the voltage at the node point B (may be referred to as "B-point voltage" hereinafter) increases. On the other hand, when the exhaust gas is rich, since a current flows from the S– terminal to the S+ terminal, the B-point voltage decreases.

The application voltage control circuit 35 monitors the B-point voltage, determines a voltage to be applied to the sensor element 10 on the basis of the monitored B-point voltage (for example, in accordance with the application-voltage characteristic line LX shown in FIG. 3), and controls the voltage of a node point D by use of the operational amplifier 34 in accordance with the determined voltage. However, in a case where the air-fuel ratio is detected only near the stoichiometric point of the exhaust gas, the voltage of the node point D may be fixed.

The node point B is connected to the non-inverting input terminal of the amplifier circuit 37, and the node point A is connected to the inverting input terminal of the amplifier circuit 37 through a resistor. The output of the amplifier circuit 37 is applied to an A/D input terminal of the microcomputer 20 as the A/F output voltage. The microcomputer 20 calculates the A/F value on the basis of the A/D-converted value of the A/F output voltage.

It sometimes occurs that moisture or organic matter adheres to the sensor element 10 before it starts to operate, that is, before the engine is started. This causes drift in the sensor output (rich error, or rich drift) during a period immediately after the sensor starts to operate. If such a rich drift occurs, the timing of determination of the A/F sensor having entered its active state is delayed, since it takes a long time for the rich drift to disappear.

For example, since the temperature in the exhaust pipe decreases after the engine is stopped, moisture remaining in the exhaust pipe deposits therein. In this case, if the exhaust gas contains organic matter that contains hydroxy groups (OH), it easily solves in the deposited water because of its high water solubility, and adheres to the diffusion resistance layer 12, inner wall of the exhaust gas chamber 17, or exhaust-gas-side electrode 15 of the sensor element 10. After the engine is started, the organic matter is carbonized by the heat generated by the heater energized, and the carbonized organic matter also adheres to the exhaust gas chamber 17. These cause oxygen in the atmosphere duct 18 to move from the atmosphere duct 18 to the exhaust gas chamber 17 due to the characteristic of zirconia ($ZrO_2$) irrespective of the gas atmosphere after startup of the engine (after activation of the sensor element), as a result of which the rich drift occurs. The rich drift becomes larger as the humidity in the exhaust pipe before engine start increases.

Particularly in recent years, there is a tendency that moisture remaining in exhaust gas after an engine is stopped increases due to improvements made to the engine, which increases the need to take measures against the rich drift. In more detail, there is tendency that the temperature of exhaust gas increases, because of expansion of an air-fuel ratio detection region, and attempts made to improve fuel economy, etc., as exampled below. When cooling performance of an engine block is increased, since the temperature of its exhaust port does not increase much, moisture contained in exhaust gas easily deposits in an exhaust pipe. A technique to integrate an exhaust manifold with an engine block is being developed, and if such a technique is used, it is expected that moisture which deposits in an exhaust pipe will increase, because the temperature of the exhaust manifold does not increase much due to cooling effect of engine cooling water. If combustion technique is improved to increase fuel efficiency, moisture contained in exhaust gas increases. If alternative fuel such as ethanol fuel is used, moisture produced by combustion increases compared to using gasoline. If moisture in an exhaust pipe increases for the reasons as exampled above, the amount of organic matter soluble in water increases eventually.

Figure 4A:
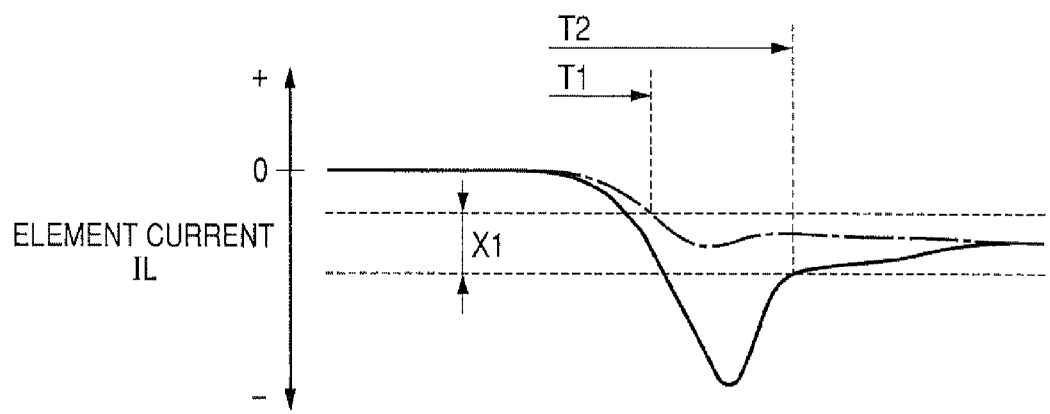
FIGS. 4A and 4B are time charts for explaining rich drift occurring during a period immediately after the A/F sensor starts operation.
Figure 4B:
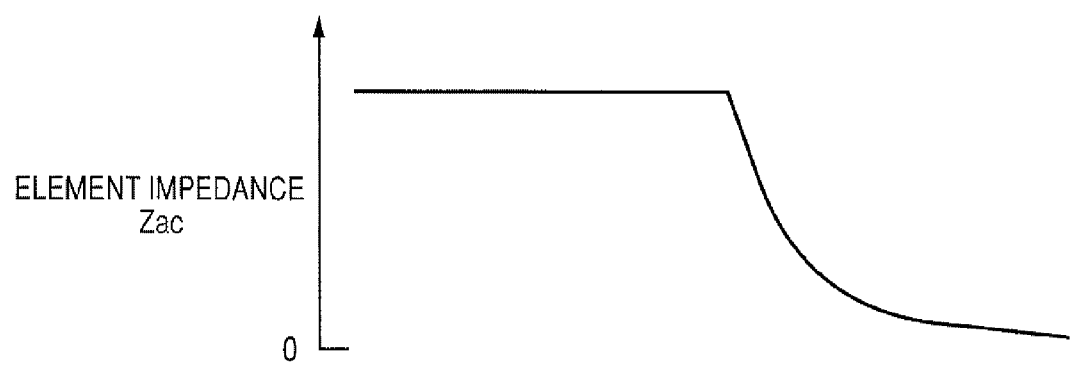

Next, the rich drift occurring during a period immediately after the start of sensor operation (immediately after the A/F sensor starts to operate) is explained with reference to the time chart shown in FIGS. 4A and 4B. The time chart of FIG. 4A shows a variation with time of the element current IL, and FIG. 4B shows a variation with time of an element impedance Zac, after the A/F sensor starts operation. FIG. 4A shows a case where fuel control is performed such that a fuel injection amount is increased from the time of engine start so that A/F becomes rich (A/F becomes 14, for example). When the A/F sensor starts operation, power supply to the heater is started. The time chart shown in FIG. 4B shows temporal variation of the element impedance Zac after the element temperature rises to such a level that the microcomputer can calculate the element impedance Zac.

As shown in FIG. 4A, the element current IL is 0 (equivalent to the stoichiometric ratio), immediately after the start of sensor operation, and thereafter it gradually shifts towards negative side (rich side). If it is assumed that there occurs no rich shift due to moisture or organic matter present in the exhaust pipe, the element current IL varies over time following the chain line shown in FIG. 4A with the activation of the A/F sensor (with the lowering of the element impedance), and finally converges to a value equivalent to the value of 14 of A/F. In this assumption, the time for the element current IL converges within a normal range (X1 in FIG. 4A) is T1.

However, when moisture or organic matter is deposited in the sensor element, the element current IL greatly shifts to the rich side as shown by the solid line in FIG. 4A. Accordingly, the time needed for the element current IL to converge to the value equivalent to the value of 14 of A/F is lengthened. As a result, the time needed for the element current IL to converge within the normal range becomes T2 (>T1).

To cope with this, in this embodiment, the application voltage (the voltage of the exhaust-gas-side electrode 15 being positive, the voltage of the atmosphere-side electrode 15 being negative) is temporarily applied between the exhaust-gas-side electrode 15 and the atmosphere-side electrode 16, at the start of sensor operation in order to forcibly supply oxygen from the atmosphere duct 18 to the exhaust gas chamber 17. This makes it possible to quickly remove moisture or organic matter deposited on the diffusion resistance layer 12 or the inner wall of the exhaust gas chamber 17.

The sensor control circuit 30 shown in FIG. 1 is provided with the switch circuit 38 between an element current measuring point (the node point B) and the application voltage control circuit 35. The switch circuit 38 is switched in accordance with a switch control command received from the microcomputer 20. Normally, a movable contact s0 is connected to a stationary contact s1 in the switch circuit 38 in order to perform normal control of the A/F sensor. In this state (may be referred to as "s1-connection state" hereinafter), the B-point voltage is inputted to the application voltage control circuit 35 so that the application voltage is variably adjusted in accordance with the B-point voltage. On the other hand, when the movable contact s0 is connected to a stationary contact s2, a constant negative voltage Vn is inputted from the negative voltage source 39 to the application voltage control circuit 35. In this state (may be referred to as "s2-connection state" hereinafter), the application voltage is set in accordance with the constant negative voltage Vn irrespective of the B-point voltage. As explained above, the normal control is performed on the A/F sensor when the switch circuit 38 is switched in the s1-connection state, while on the other hand, the negative voltage control is performed on the A/F sensor when the switch circuit 38 is switched in the s2-connection state.

FIG. 5A and FIG. 5B are schematic cross-sectional views of the sensor element 10 for further explaining the application voltage control (the normal control and the negative voltage control) performed on the A/F sensor. FIG. 5A shows the case where the normal control is performed, and FIG. 5B shows the case where the negative voltage control is performed.

In the normal control, as shown in FIG. 5A, a positive voltage (0.4 V, for example) is applied as the application voltage VP between the exhaust-gas-side electrode 15 and the atmosphere-side electrode 16, the voltage of the exhaust-gas-side electrode 15 being negative, the voltage of the atmosphere-side electrode 16 being positive. At this time, the application voltage VP is set in accordance with the output characteristic (V-I characteristic) of the sensor element 10 shown in FIG. 3. By the application of the positive application voltage VP, oxygen ions move from the atmosphere-side electrode 16 to the exhaust-gas-side electrode 15 through the solid electrolyte layer 11 due to the characteristic of zirconia. As a result, oxygen is supplied to the exhaust gas chamber 17 from the atmosphere duct 18, and accordingly, organic matter on the side of the exhaust gas chamber 17 is oxidized and removed quickly. However, since the application voltage VP is positive, the supply amount of oxygen to the exhaust gas chamber 17 is relatively small in the normal control.

In the negative voltage control, as shown in FIG. 5B, a negative voltage (−0.4 V, for example) is applied as the application voltage VP between the exhaust-gas-side electrode 15 and the atmosphere-side electrode 16, the voltage of the exhaust-gas-side electrode 15 being positive, the voltage of the atmosphere-side electrode 16 being negative. By the application of the negative application voltage VP, oxygen ions move from the atmosphere duct 18 to the exhaust gas chamber 17 due to the characteristic of zirconia, and also due to the pumping operation by the negative voltage application. By the negative voltage application, the oxygen ion movement from the atmosphere-side electrode 16 to the exhaust-gas-side electrode 15 is promoted. As a result, oxygen supply to the side of exhaust gas chamber 17 is promoted, and accordingly, organic matter on the side of the exhaust gas chamber 17 is oxidized and removed quickly.

Figure 6:
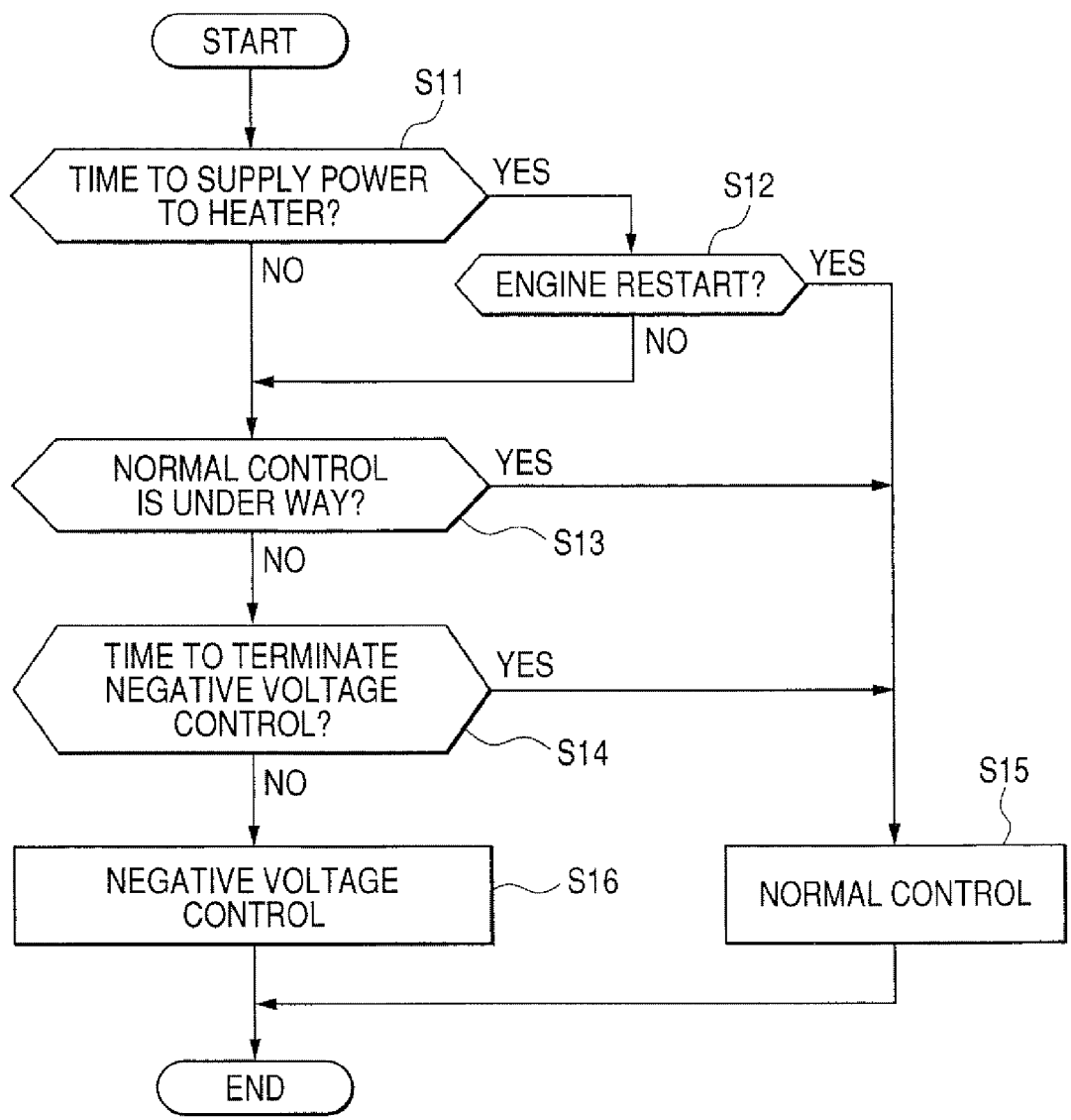
FIG. 6 is a flowchart showing processes of the voltage application control at the time of engine start.

Next, the process of the application voltage control is explained in more detail with reference to the flowchart of FIG. 6. This process is performed repeatedly at regular time intervals by the microcomputer 20.

This process begins by determining at step S11 whether or not it is time to supply power to the heater. For example, if an ignition switch is detected to just have been turned on, it is determined that it is time to supply power to the heater. When the determination result at step S11 is YES, the process proceeds to step S12. At step S12, it is determined whether or not it is time to restart the engine. For example, if the time elapsed from the time when the engine was stopped (when the ignition switch was turned off) is less than a predetermined time, or if the temperature of engine cooling water is higher than a predetermined temperature, it is determined that it is time to restart the engine. If the determination result at step S11 is NO, or if the determination result at step S12 is NO, the process proceeds to step S13. If the determination result at step S12 is YES, the process proceeds to step S15. Incidentally, if the determination result at step S11 is YES, and the determination result at step S12 is NO, it can be determined that it is time to cold-starts the A/F sensor.

At step S13, it is determined whether or not the normal control already has been under way as the application voltage control.

If the determination result at step S13 is NO, the process proceeds to step S14, and otherwise proceeds to step S15.

At step S15, the switch circuit 38 is switched so that the normal control is performed as the application voltage control. More specifically, the switch circuit 38 is switched in the s1-connection state so that the application voltage control circuit 35 can control the application voltage in accordance with the sensor current IL measured at every moment of time, on the basis of the output characteristic of the sensor element 10 shown in FIG. 3.

At step S14, it is determined whether or not it is time to terminate the negative voltage control. For example, if the element impedance Zac monitored after the start of sensor operation is detected to be larger than a predetermined threshold TH, it is determined that it is not yet the time to terminate the negative voltage control, and if the element impedance Zac is detected to be equal to or smaller than the threshold TH, it is determined that it is time to terminate the negative voltage mode. The threshold TH is set to a value (600Ω, for example) larger than the impedance value (30-40Ω) which the sensor element 10 takes when it has entered the active state.

Next, the procedure for calculating the element impedance Zac is explained briefly. In this embodiment, the so-called sweep technique is used to calculate the element impedance Zac. In this technique, the microcomputer 20 temporarily changes the voltage applied to the sensor element 10 to an alternating voltage, and calculate the element impedance Zac on the basis of variation of the element current in this state. In more detail, the application voltage (the D-point voltage) is varied, for example, by 0.2 V, towards positive and negative sides alternately by use of a sweep circuit (or by use of the application voltage control circuit 35), and a variation of the B-point voltage in this state is measured. When the variation of the application voltage is $\Delta V$, and a measured variation of the element current is $\Delta I$, the element impedance Zac can be calculated as $\Delta V/\Delta I$. Alternatively, the element impedance Zac may be calculated on the basis of a variation of the element current and a variation of the application voltage when the element current is varied towards positive and negative sides alternately.

At step S16, the switch circuit 38 is switched so that the negative voltage control is performed as the application voltage control. More specifically, the switch circuit 38 is switched in the s2-connection state, so that the negative voltage Vn generated by the negative voltage source 39 is applied to the sensor element 10, to thereby forcibly supply oxygen from the atmosphere duct 18 to the exhaust gas chamber 17.

The negative voltage control is performed until the determination result at step S14 becomes YES, after which the negative voltage control is switched to the normal control.

In the above, it has been described that step S14 uses the element impedance Zac to determine whether it is time to terminate the negative voltage control, however, this determination may be made by any of the following procedures.

(1) An integration value of the element current IL integrated from the time of the start of sensor operation is calculated, and when the integration value reaches a predetermined threshold, it is determined that it is time to terminate the negative voltage control. In this procedure, any one of the following options may be used.

(a) Integrating a value of the element current IL from the time when the A/F sensor starts operation.

(b) Integrating a value of the element current IL from the time when the element current IL starts to vary with the increase of the temperature of the sensor element after the A/F sensor starts operation.

(c) Integrating a value of the element current IL from the time when the element current IL reaches a normal level which the element current IL should take in a normal state (converged state) after the element current IL starts to vary with the increase of the temperature of the sensor element after the start of sensor operation.

(2) An integration value of the power supplied to the heater integrated from the time of the start of sensor operation is calculated, and when the integration value reaches a predetermined threshold, it is determined that it is time to terminate the negative voltage control.

(3) A variation of the resistance of the heater is monitored after the start of sensor operation, and when the monitored resistance exceeds a predetermined threshold, it is determined that it is time to terminate the negative voltage control.

(4) When a predetermined time has elapsed since the start of sensor operation, it is determined that it is time to terminate the negative voltage control.

Incidentally, when the A/F sensor is in cold condition, since the internal resistance of the sensor element 10 is at its maximum, the calculation of the element impedance Zac cannot be performed until the temperature of the sensor element rises to a certain level. Accordingly, to determine the timing to terminate the negative voltage control on the basis of the element impedance Zac, it is necessary to wait until the temperature of the sensor element 10 rises to a level which enables calculating the element impedance Zac. However, according to any of the above procedures (1) to (4), it is possible to determine the timing to terminate the negative voltage control without waiting until the temperature of the sensor element 10 rises to such a level.

In the above, it has been described that the negative voltage control is started when power supply to the heater is started. However, the timing to start the negative voltage control may be modified. For example, the negative voltage control may be started at the timing when the element current IL starts to vary after the start of sensor operation.

Figure 7:
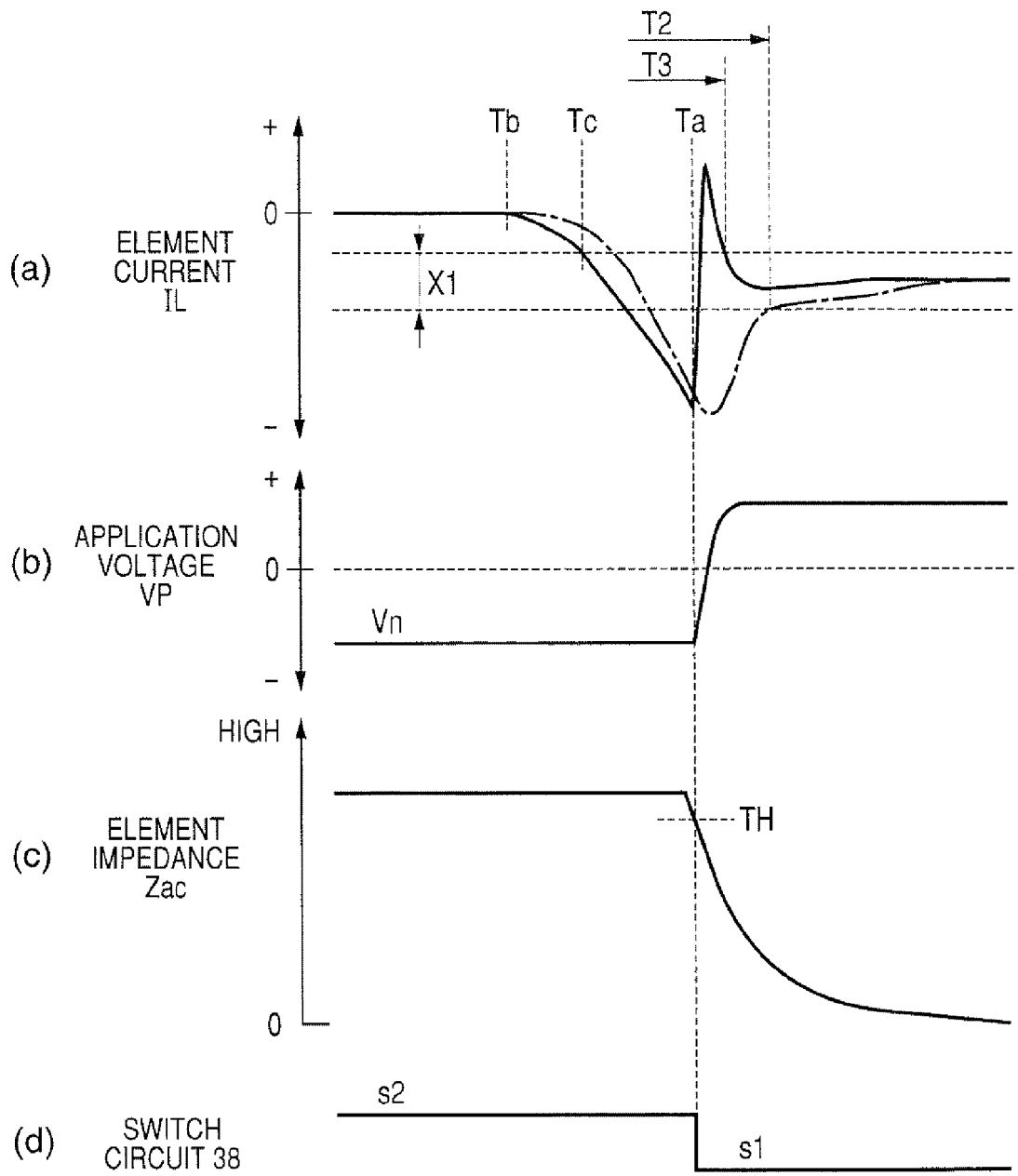
FIG. 7 is a time chart showing variations with time of an element current etc., when a negative voltage control is performed on the A/F sensor by the gas sensor control apparatus shown in FIG. 1.

An example of variation with time of the element current IL when the negative voltage control is started at such a modified timing is explained with reference to FIG. 7. In FIG. 7, (a) shows a variation with time of the element current IL after the start of sensor operation, (b) shows a variation with time of the application voltage VP, (c) shows a variation with time of the element impedance Zac, and (d) shows a progression of a switch state of the switch circuit 38. In (a) of FIG. 7, the chain line represents a variation with time of the element current IL in the case where the normal control is performed, which is the same as that shown in FIG. 4A.

As seen from (a) in FIG. 7, in this example, since the negative voltage Vn (−0.4 V, for example) is applied to the sensor element 10 as soon as the A/F sensor starts operation, the variation of the element current IL shifts more to the negative side as shown by the solid line compared to that in the case where the normal control is performed. This is because oxygen is forcibly supplied from the atmosphere duct 18 to the exhaust gas chamber 17, as a result of which the element current IL additionally includes a negative component due to the forcibly supplied oxygen. Since the internal DC resistance Ri of the sensor element 10 decreases with the increase of the element temperature after the A/F sensor starts operation, the element current IL gradually shifts to the negative side with the decrease of the internal DC resistance Ri of the sensor element 10, even though the negative application voltage is constant.

Figure 8:
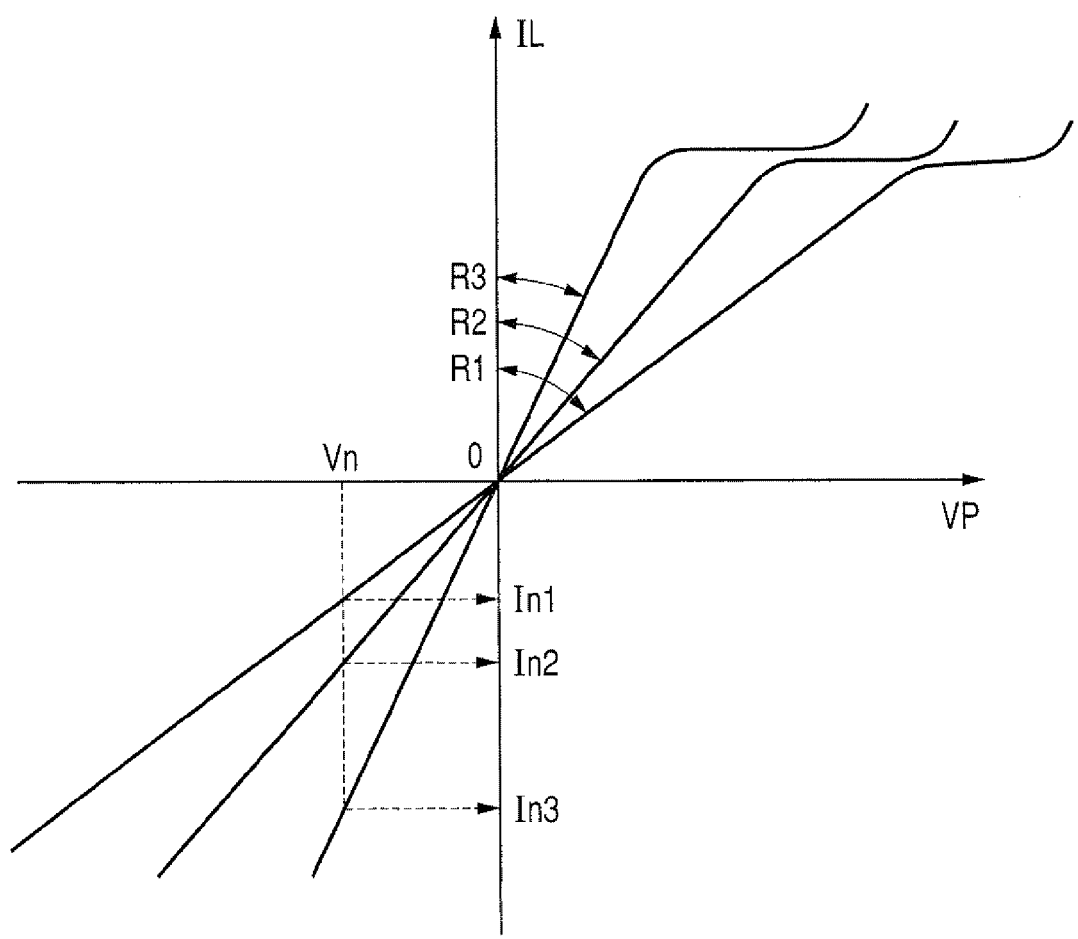
FIG. 8 is a graph showing an output characteristic of the A/F sensor.

The variation with time of the element current IL when the negative voltage control is performed is further explained with reference to FIG. 8. FIG. 8 shows resistance dominant regions of the sensor output characteristic (V-I characteristic) in three cases different in the internal DC resistance Ri. As shown in FIG. 8, when the DC resistance Ri gradually decreases as R1→R2→R3, the slopes of the resistance dominant regions gradually increase. Accordingly, even though the application voltage VP is kept constant at Vn, the element current IL gradually shifts to the negative side as In1→In2→In3.

Returning to FIG. 7, the negative voltage is switched to the normal application voltage at the timing Ta at which the element impedance Zac lowers below the threshold TH. More specifically, the switch circuit 38 is switched from the s2-connect state to the s1-connect state. As a result, the application voltage is switched from negative to positive, and accordingly, the element current IL sharply shifts to the positive side, and then converges to a certain current value depending on the A/F at the time. After the timing Ta, the application voltage VP is set to a voltage in accordance with the element current IL at every moment of time. In the case of FIG. 8, the application voltage VP is set to a positive voltage corresponding to the case of the A/F being 14.

When the normal control is performed, the time needed for the element current IL to converge within the normal output range (X1 in FIG. 7) is T2. On the other hand, when the negative voltage control is performed, it is reduced to T3.

Incidentally, in the case where the timing to terminate the negative voltage control (the timing to switch from the s2-connection state to the s1-connection state in the switch circuit 38) is determined on the basis of the integration value of the element current IL integrated from the time of the start of sensor operation, the integration value may be calculated by integrating a value of the element current IL from the time when the element current starts to vary with the increase of the element temperature (after the timing Tb in FIG. 7). Alternatively, the integration value may be calculated by integrating a value of the element current IL from the time when the element current IL reaches a normal level which the element current IL should take in a normal state (converged state) after the element current IL starts to vary with the increase of the element temperature after the start of sensor operation (after the timing Tc in FIG. 7).

The above described first embodiment of the invention provides the following advantages.

The above first embodiment has the structure in which the negative voltage control is performed when the A/F sensor starts operation to excessively supply oxygen to the exhaust gas chamber 17. This makes it possible to early remove moisture or organic matter present in the exhaust gas chamber 17 before the start of sensor operation. Accordingly, it is possible to reduce the delay of the sensor activation due to the rich drift at the start of sensor operation. Hence, according to the first embodiment, it becomes possible that the element current IL early reaches a normal level, and accordingly the activation of the A/F sensor can be determined early.

The above first embodiment has the structure in which the negative voltage control is started at the timing when power supply to the heater is started so that the negative voltage control is performed during the period in which the temperature of the sensor 10 increases. In this structure, the negative voltage control is performed during a period before the sensor output reaches a normal level (that is, while the sensor output cannot be used yet). Since no disadvantage occurs even if the sensor output greatly varies during this period, the negative voltage control can be performed without any problem during this period.

By starting the negative voltage control when the A/F sensor starts operation, and thereafter switching from the negative voltage control to the normal control, it becomes possible to make an early start the normal control of the A/F sensor.

The above first embodiment is configured such that when the element impedance Zac reaches a predetermined threshold, the negative voltage control is terminated, and then the normal control is started. This makes it possible to adjust the timing to terminate the negative voltage control in accordance with the progression of the activation of the sensor element 10. Accordingly, this configuration makes it possible to prevent the oxygen supply to the exhaust gas chamber 17 from becoming excessive or inadequate.

The above first embodiment may be so modified that a voltage intermediate between the application voltage in the negative voltage control and the application voltage in the normal control is applied between the electrodes of the sensor element during the control transition period in which the negative voltage control is switched to the normal control, in order to suppress the element current IL from steeply shifting (tailing) to the positive side during the transition period. For example, the negative voltage Vn may be gradually varied during the control transition period as shown in any one of (b), (c), and (d) in FIG. 9.

Figure 9:
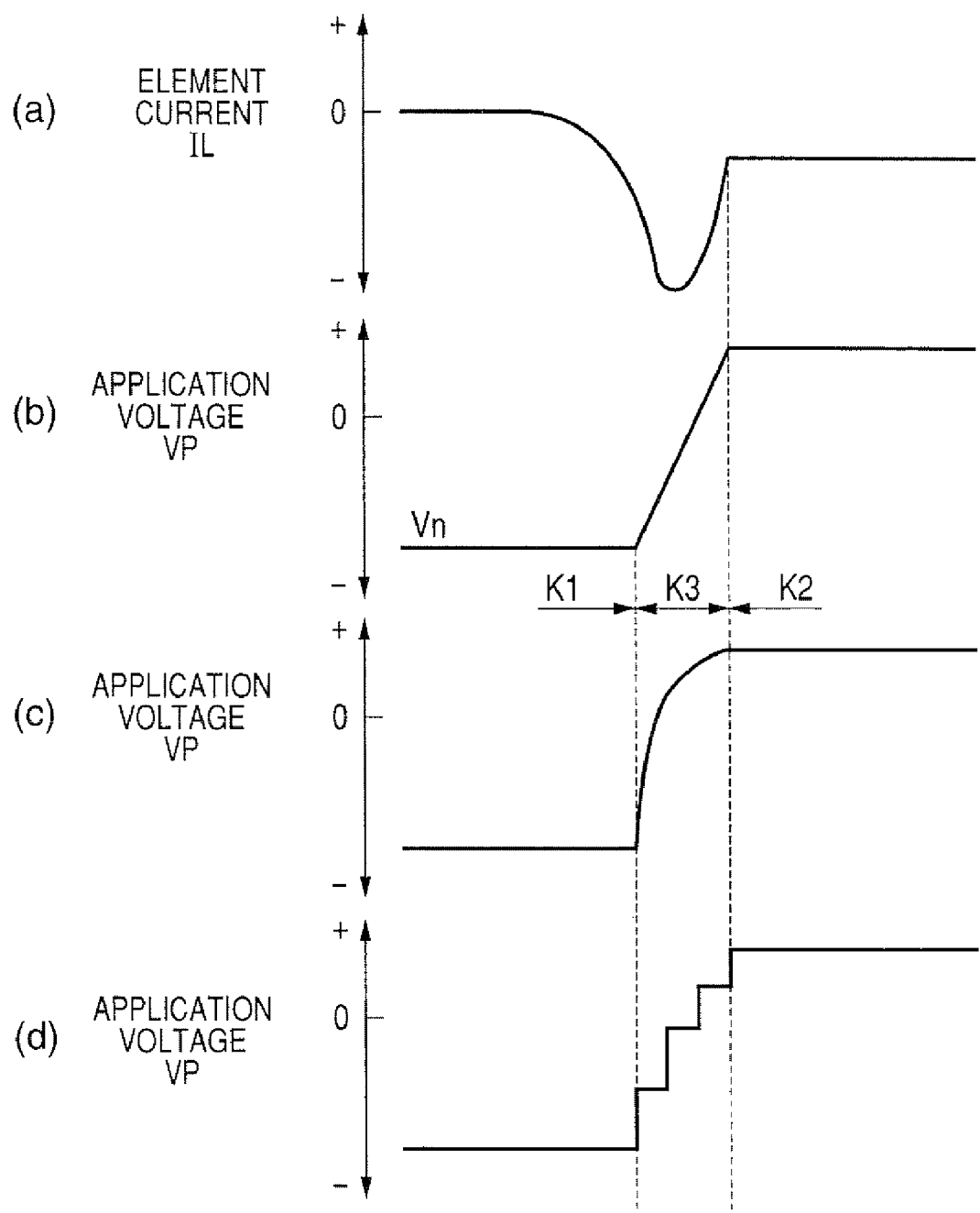
FIG. 9 is a time chart showing variations with time of an element current etc., when the negative voltage control is performed on the A/F sensor by a modification of the gas sensor control apparatus shown in FIG. 1.

In FIG. 9, K1 denotes the period of the negative voltage control, K2 denotes the period of the normal control, and K3 denotes the control transition period. In (b) of FIG. 9, the application voltage Vp is continuously varied over the control transition period at a constant rate from the negative voltage Vn used in the negative voltage control to a voltage used in the normal control. By varying the application voltage Vp as above, the element current IL can be suppressed from steeply shifting during the control transition period.

The negative voltage control may be terminated by switching the switch circuit 38 to the s1-connection state at the timing of start of the control transition period in which the application voltage control circuit 35 gradually varies the application voltage VP.

As shown (c) in FIG. 9, the application voltage VP may be gradually varied at a rate decreasing with time. Also, the application voltage VP may be gradually varied at a rate increasing with time. As shown in (d) in FIG. 9, the application voltage VP may be varied stepwise with decreasing step size. Also, the application voltage VP may be varied stepwise with increasing step size. According to any of the above described ways of gradually varying the application voltage VP, it is possible to suppress the element current IL from steeply shifting.

Second Embodiment

Next, a second embodiment of the invention is described.

Figure 10:
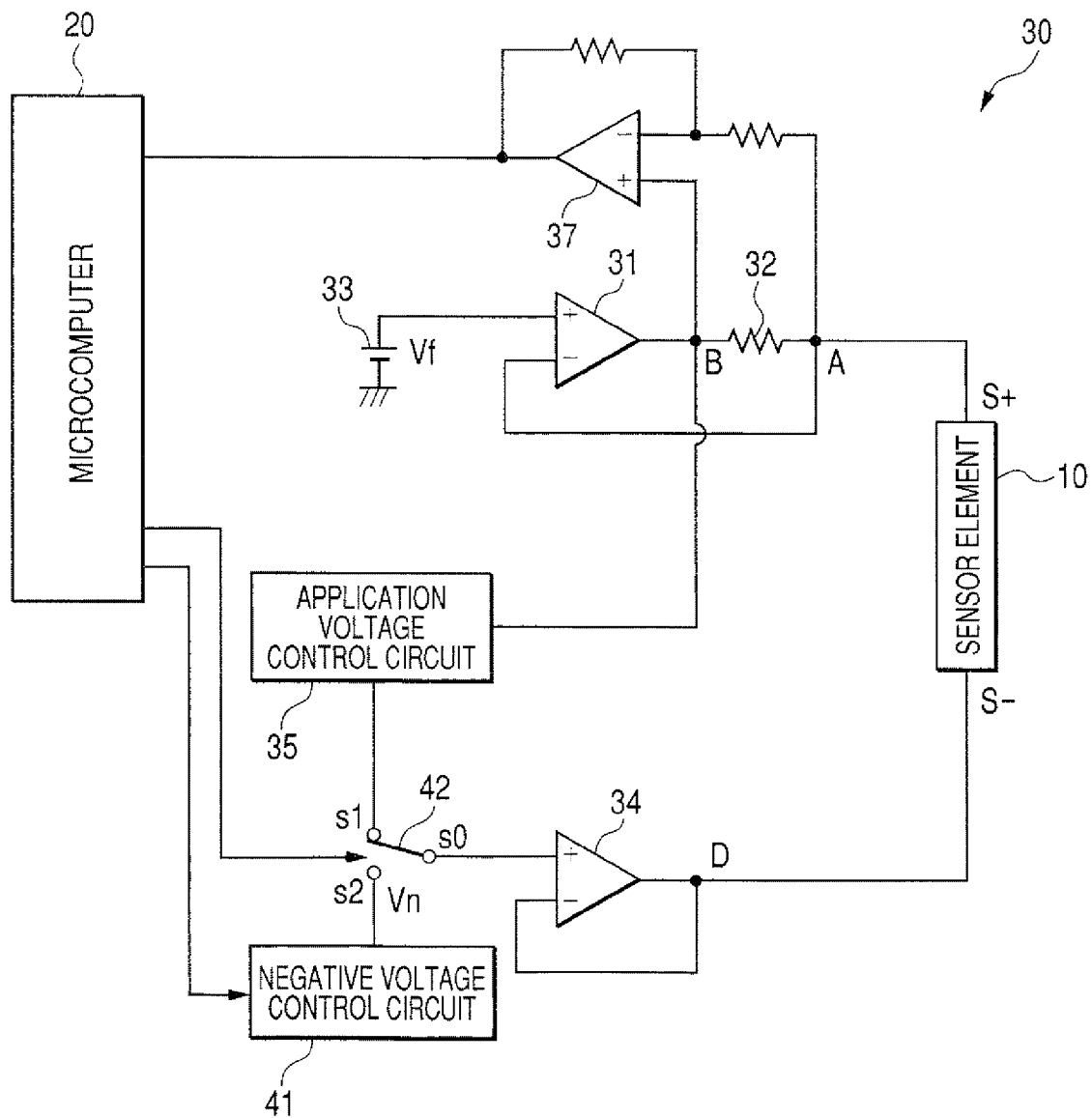
FIG. 10 is a circuit diagram of a sensor control circuit of a gas sensor control apparatus according to a second embodiment of the invention.

FIG. 10 is a diagram showing a circuit structure of a sensor control circuit 30 of a gas sensor control apparatus according to a second embodiment of the invention. As shown in FIG. 10, compared to the sensor control circuit 30 of the first embodiment, the sensor control circuit 30 of the second embodiment is additionally provided with a negative voltage control circuit 41, and provided with a switch circuit 42 instead of the switch circuit 38. This switch circuit 42 enables selecting between the application voltage control circuit 35 and the negative voltage control circuit 41 to perform the application voltage control on the A/F sensor. When the switch circuit 42 is switched in the s1-connection state, the application voltage control is performed by the application voltage control circuit 35, and when the switch circuit 42 is switched in the s2-connection state, the application voltage control is performed by the negative voltage control circuit 41. Each of the negative voltage control circuit 41 and the switch circuit 42 is supplied with a control command form the microcomputer 20.

After the start of sensor operation, the DC resistance Ri of the sensor element gradually decreases with the increase of the element temperature, and the element current IL shifts more towards the negative side with this decrease of the DC resistance Ri even when the application voltage is kept constant. Since if the element current IL shifts towards the negative side beyond a certain limit value, the sensor element may be broken, it is preferable to set the negative voltage Vn to such a value that the element current IL does not shift beyond the limit value. The limit value depends on the volume of the atmosphere duct 18, that is, depending on the oxygen supply capacity of the atmosphere duct 18. Accordingly, when the volume of the atmosphere duct 18 is reduced, the limit value is set smaller by that amount.

Immediately after the start of sensor operation, the element current IL is hard to reach the limit value on the negative side, because the DC resistance Ri is large immediately after the start of sensor operation. Accordingly in this embodiment, the negative voltage Vn is set such that the absolute value thereof is large immediately after the start of sensor operation, and thereafter gradually decreases to shift to the 0 V side. This makes it possible to prevent the element current IL from reaching the limit value on the negative side when the temperature of the sensor element increases, while ensuring adequate oxygen supply to the exhaust gas chamber 17.

Figure 11:
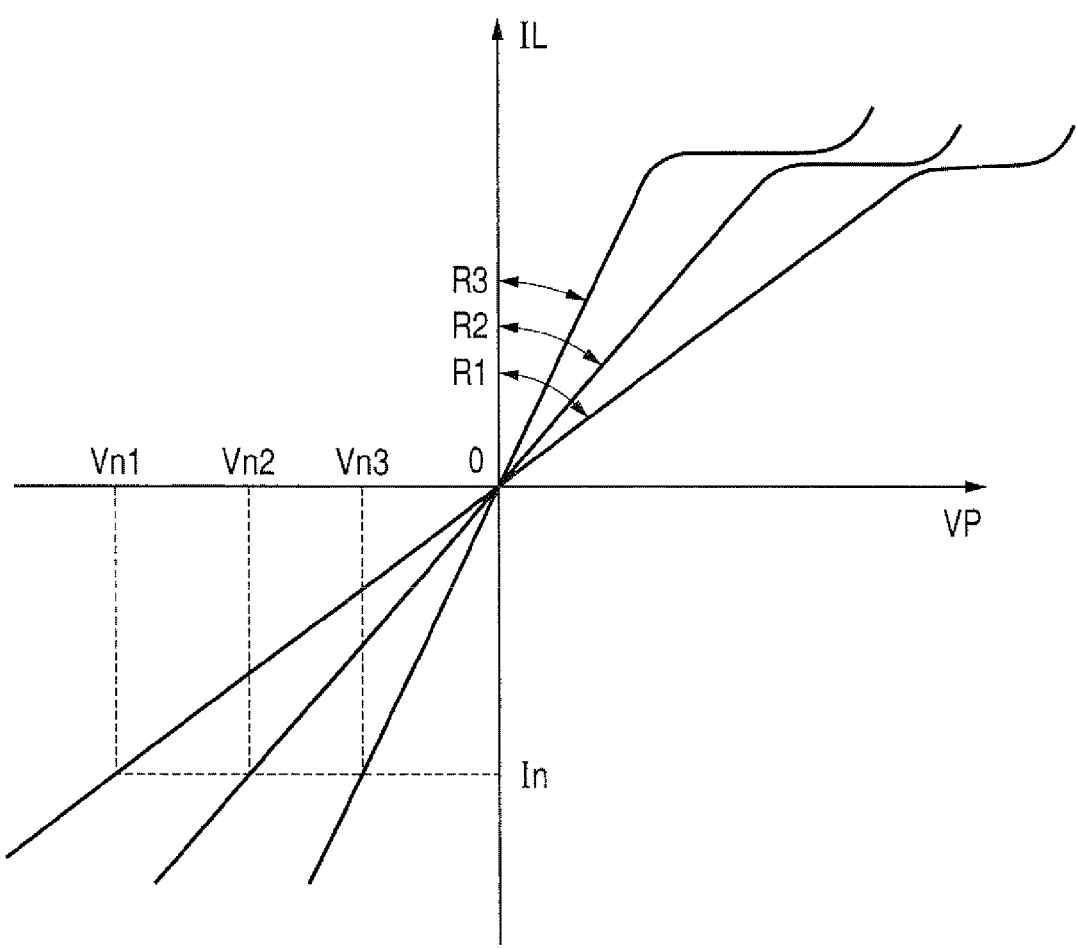
FIG. 11 is a graph showing an output characteristic of an A/F sensor controlled by the gas sensor control apparatus shown in FIG. 10.

FIG. 11 shows resistance dominant regions of the sensor output characteristic (V-I characteristic) in three cases different in the internal DC resistance Ri. As shown in FIG. 11, when the DC resistance Ri gradually decreases as R1→R2→R3 with the increase of the element temperature, the negative voltage Vn is gradually decreased as Vn1→Vn2→Vn3. As a result, the element current IL is kept at a nearly constant value In.

In the negative voltage control circuit 41, the negative voltage Vn is variably set as a function of elapsed time during the negative voltage control period after the start of sensor operation. More specifically, the negative voltage Vn is variably set as a function of elapsed time obtained by referring to an expected variation with time of the DC resistance Ri after the start of sensor operation, the expected variation being calculated and stored in advance.

There is a correlation between a supply amount of electric power supplied to the heater 19 and the DC resistance Ri. Accordingly, it is possible to variably set the negative voltage Vn on the basis of the supply amount of electric power (integrating electric power).

FIG. 12 is a time chart showing a variation with time of the element current IL when the negative voltage control in which the negative voltage Vn is variably set is performed. In FIG. 12, (a) shows a variation with time of the element current IL after the start of sensor operation, (b) shows a variation with time of the application voltage VP, (c) shows a variation with time of the DC resistance Ri, and (d) shows a transition of the switch state of the switch circuit 42.

As shown in (c) in FIG. 12, the DC resistance Ri of the sensor element gradually decreases after the start of sensor operation (after power supply to the heater is started). With the start of sensor operation, the switch circuit 42 is switched in the s-2 connection state, and accordingly, the sensor element 10 is applied with the negative voltage V by the negative voltage control circuit 41 from the start of sensor operation. At this time, the negative voltage Vn is set to a relatively large value (−2.0 V, for example), and thereafter, gradually decreased towards 0 V.

Incidentally, since the element current IL is kept at 0 mA for a certain period immediately after the start of sensor operation irrespective of the value of the application voltage VP, the negative voltage Vn may be kept at a constant value over the certain period immediately after the start of sensor operation.

As explained above, by applying the negative voltage Vn set at the relatively large value (−2.0 V, for example) to the sensor element 10, the element current IL takes a large negative value at an early stage. This has the effect to further promote the oxygen supply from the atmosphere duct 18 to the exhaust gas chamber 17. The increase rate of the negative voltage Vn is kept temporarily at a nearly constant value, because the DC resistance Ri decreases causing the negative voltage Vn to gradually vary towards 0 V. Thereafter, when it comes time to terminate the negative voltage control, the switch circuit 42 is switched from the s2-connection state to the s1-connection state, to thereby switch from the negative voltage control to the normal control.

According to the above described second embodiment in which the negative voltage Vn is variably controlled after the start of sensor operation, it is possible to adjust the element current which flows with the application of the negative voltage Vn to the sensor element. As described above, by gradually decreasing the negative voltage Vn with the variation of the DC resistance Ri of the sensor element 10, it becomes possible to keep the element current IL (negative current) at a nearly constant value. As a result, the oxygen supply to the exhaust gas chamber 17 can be performed appropriately, while preventing the element current IL becoming excessively large to the negative side.

Third Embodiment

Figure 13A:
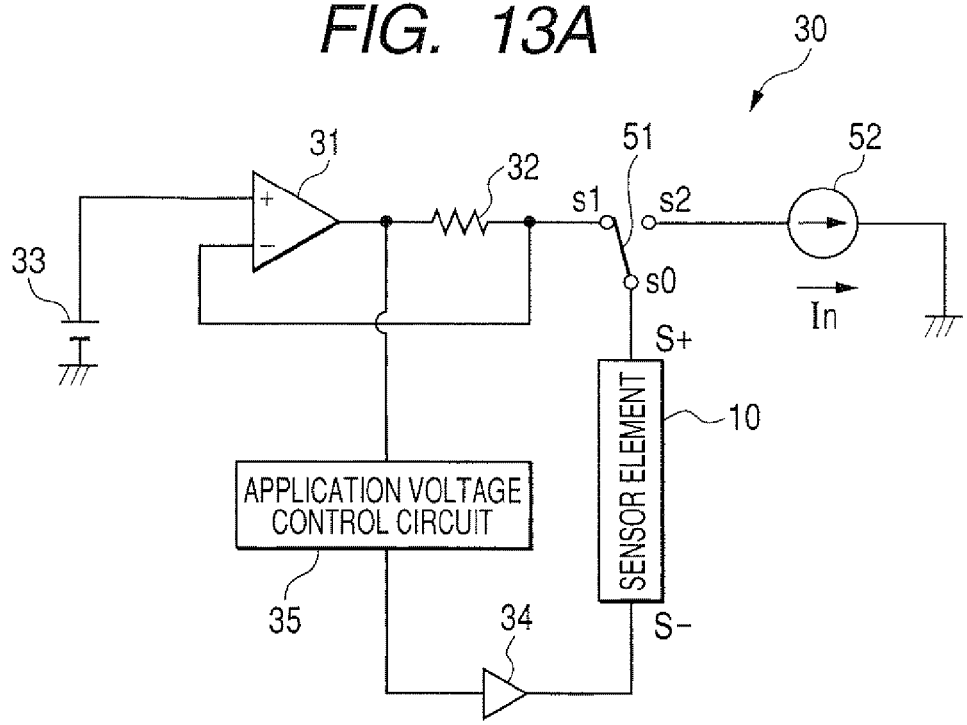
FIG. 13A is a circuit diagram of a sensor control circuit of a gas sensor control apparatus according to a third embodiment of the invention.
Figure 13B:
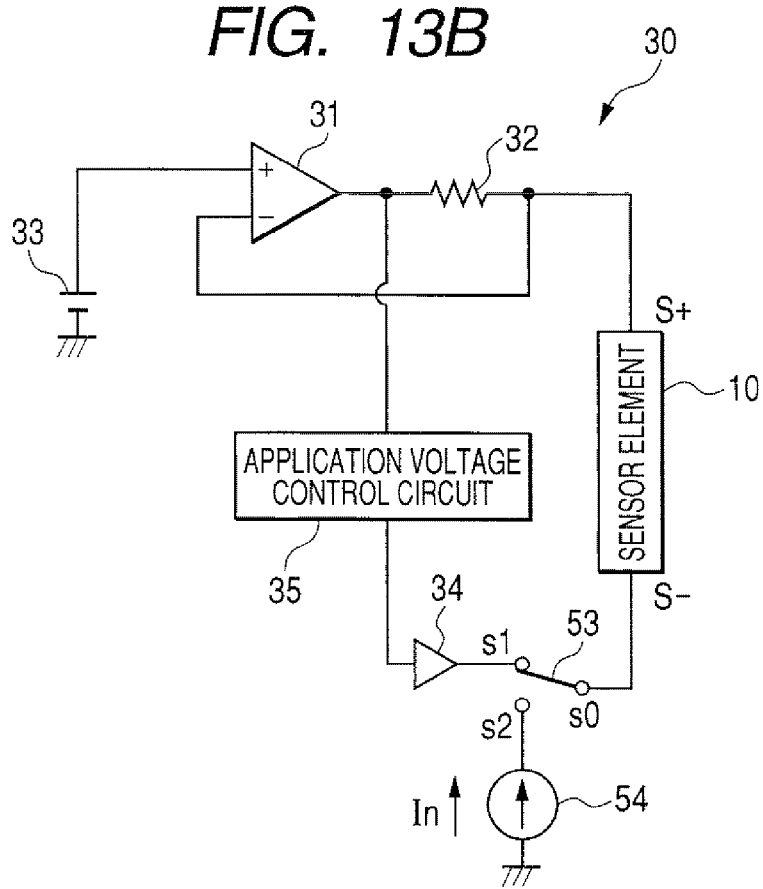
FIG. 13B is a circuit diagram of a modification of the sensor control circuit shown in FIG. 13A.

Next, a third embodiment of the invention is described. FIG. 13A is a circuit diagram of a sensor control circuit 30 of a gas sensor control apparatus according to a third embodiment of the invention, and FIG. 13 B is a circuit diagram of a modification of the sensor control circuit 30 shown in FIG. 13A. In FIGS. 13A and 13B, the same reference characters as those in FIG. 1 indicate the same or corresponding components shown in FIG. 1, and some of the components common to the first and second embodiments (the microcomputer 10, for example) are omitted from being shown.

As shown in FIG. 13A, the positive terminal (S+ terminal) of the sensor element 10 is connected with a switch circuit 51. The switch circuit 51 is switched in accordance with a switch command signal from the microcomputer (omitted from being shown). Normally, the switch circuit 51 is switched in the s1-connection state in order to perform the normal control on the A/F sensor. When, the switch circuit 51 is switch in the s2-connection state, the positive terminal (S+ terminal) of the sensor element 10 is connected with a constant current circuit 52. By the operation of the constant current circuit 52, which is a current drawing type circuit, a negative current In flows in the direction from the exhaust-gas-side electrode 15 (S−) to the atmosphere-side electrode 16 (S+).

As shown in FIG. 13B, the modification of the sensor control circuit 30 of FIG. 13A includes a switch circuit 53 and a constant current circuit 54 instead of the switch circuit 51 and the constant current circuit 52. By the operation of the constant current circuit 54, which is a current discharge type circuit, the negative current In flows in the direction from the exhaust-gas-side electrode 15 (S−) to the atmosphere-side electrode 16 (S+).

Figure 14:
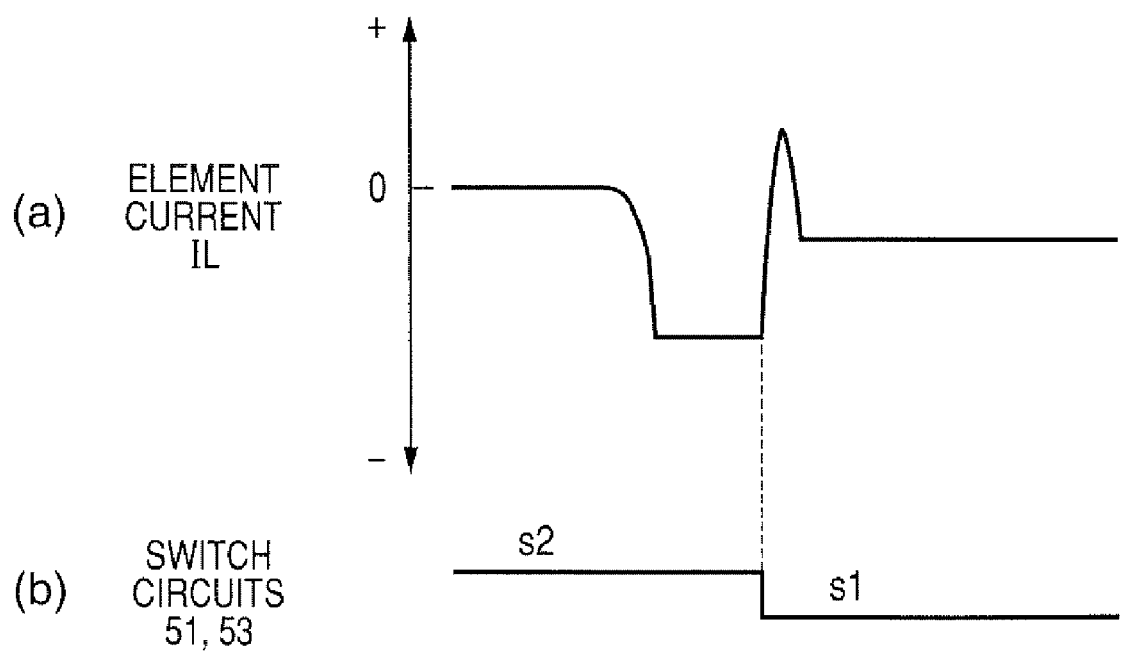
FIG. 14 is a time chart showing variations with time of an element current etc., when the negative voltage control is performed by the gas sensor control apparatus shown in FIG. 13.

FIG. 14 is a time chart showing a variation with time of the element current IL when the negative current In flows through the sensor element 10. In FIG. 14, (a) shows the variation with time of the element current IL after the start of sensor operation, and (b) shows a transition of a switch state of the switch circuits 51 and 53.

As shown in FIG. 14, with the start of sensor operation, the switch circuit 51 (or 53) is switched in the s2-connection state, as a result of which the negative current In flows through the sensor element 10 by the operation of the constant current circuit 52 (or 54). In more detail, the element current IL is kept at 0 mA for a certain period immediately after the start of sensor operation, and the negative current IL starts to flow after the element temperature rises to a certain level. By the flow of the negative current In, oxygen is forcibly supplied from the atmosphere duct 18 to the exhaust gas chamber 17. Thereafter, when it comes time to terminate the negative voltage control, the switch circuit 51 (or 53) is switched form the s2-connection state to the s1-connection state, to thereby switch from the negative voltage control to the normal control.

According to the third embodiment, it becomes possible to suppress the delay of the sensor activation due to the rich drift at the start of sensor operation, like in the first embodiment. Hence, according to the third embodiment, it is possible that the element current IL early reaches a normal level, and accordingly the activation of the A/F sensor can be determined early.

Fourth Embodiment

Figure 15:
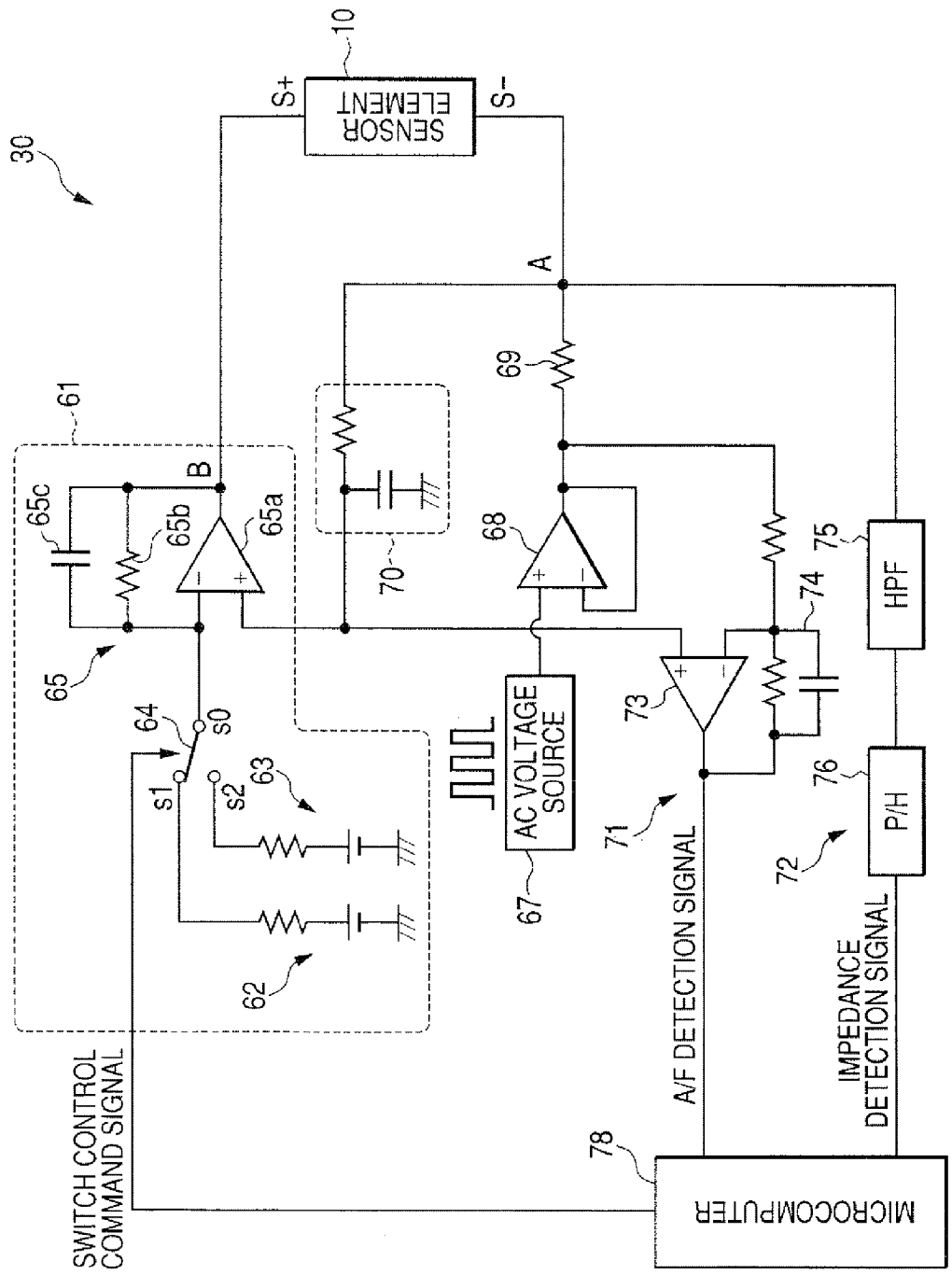
FIG. 15 is a circuit diagram of a sensor control circuit of a gas sensor control apparatus according to a fourth embodiment of the invention.

Next, a fourth embodiment of the invention is described. FIG. 15 is a circuit diagram of a sensor control circuit 30 of a gas sensor control apparatus according to a fourth embodiment of the invention.

As shown in FIG. 15, the positive terminal (S+ terminal) of the sensor element 10 is connected with an application voltage control circuit 61. The application voltage control circuit 61 includes voltage sources 62 and 63, a switch circuit 64 to select between the voltage sources 62 and 63, and a non-inverted amplifier circuit 65 whose inverted input terminal is connected to the movable contact s2 of the switch circuit 64. The non-inverted amplifier circuit 65 includes an operational amplifier 65a, a feedback resistor 65b connected between the non-inverted input terminal and the output terminal thereof, and a capacitor 65c connected in parallel to the feedback resistor 65b. Each of output resistors of the voltage sources 62 and 63 serves as an input resistor of the non-inverted amplifier circuit 65. The non-inverted amplifier circuit 65c operates as an LPF for preventing the application voltage from oscillating. The cut-off frequency fc of the LPF may be set at 2.7 Hz.

The negative terminal (S− terminal) of the sensor element 10 is connected with a series of an AC voltage source 67, a buffer 68, and a current measuring resistor 69. The AC voltage source 67 generates an AC voltage of a frequency of 10 to 20 kHz to be applied to the sensor element 10. The voltage source 67 is mainly constituted by an AC voltage generating circuit, and an LPF which filters the output to the AC voltage generating circuit. The AC voltage generated by the AC voltage source 67 has a peak-to-peak amplitude of 2 V and a DC offset of 2.2 V as a reference voltage.

The current measuring resistor 69 is provided on a current path between the AC voltage source 67 and the sensor element 10. One of the ends of the current measuring resistor 69 on the side opposite to the sensor element 10 is kept at the reference voltage (the DC offset voltage of the AC voltage generated by the AC voltage source 67). The element current is measured at a halfway point A between the current measuring resistor 69 and the negative terminal of the sensor element 10.

The halfway point A is connected with one end of a LPF 70 constituted by a resistor and a capacitor. The other end of the LPF 70 is connected to the non-inverting input terminal of the operational amplifier 65a of the non-inverting amplifier circuit 65. The voltage at the halfway point A is inputted to the non-inverting amplifier circuit 65 of the application voltage control circuit 61 through the LPF 70. The cut-off frequency fc of the LPF 70 is set to 150 Hz, for example.

The switch circuit 64 is switched in accordance with a switch control command from a microcomputer 78. Normally, the switch circuit 64 is switched in the s1-connection state in order to perform the normal control on the A/F sensor. In the normal control, the voltage of the voltage source 62 is inputted to the inverting input terminal of the operational amplifier 65a of the non-inverting amplifier circuit 65, as a result of which the output voltage of the non-inverting amplifier circuit 65 (the voltage at the point B in the drawing; may be referred to as "B-point voltage" hereinafter) is fixed at a constant voltage, 2.6 V, for example. On the other hand, when the switch circuit 64 is switched in the s2-connection state, the voltage of the voltage source 63 is inputted to the inverting input terminal of the operational amplifier 65a of the non-inverting amplifier circuit 65, as a result of which the output voltage of the non-inverting amplifier circuit 65 is fixed at a constant voltage, 1.7V, for example.

When the output voltage of the non-inverting amplifier circuit 65 (the B-point voltage) is fixed at 2.6 V, the sensor element 10 is applied with a positive voltage. On the other hand, when the output voltage of the non-inverting amplifier circuit 65 is fixed at 1.7 V, the sensor element 10 is applied with a negative voltage.

The voltage at the halfway point A (may be referred to as "A-point voltage" hereinafter) is taken in by an A/F signal output circuit 71 which outputs an A/F detection signal having a value depending on the element current, and also taken in by an impedance signal output circuit 72 which outputs an impedance detection signal having a value depending on the impedance of the sensor element. The A/F signal output circuit 71 is constituted by a non-inverting amplifier circuit including an operational amplifier 73, and a LPF 74 portion connected between the inverting input terminal and the output terminal of the operational amplifier 73. The A-point voltage is inputted to the non-inverting input terminal of the operational amplifier 73 of the A/F signal output circuit 71 through the LPF 70 which removes an AC component from the A-point voltage. The impedance signal output circuit 72 is constituted by an HPF 75 and a peak hold circuit 76. The peak hold circuit 76 is integrally provided with a signal amplifier. The A/F detection signal outputted from the A/F signal output circuit 71 and the impedance detection signal outputted from the impedance signal output circuit 72 are both inputted to the microcomputer 78.

In the sensor control circuit having the above described structure, the switch circuit 64 is switched in the s2-connection state at the time of the start of sensor operation (at the time of the start of power supply to the heater) with the start of the engine, as a result of witch the negative voltage is applied to the sensor element 10. As a consequence, oxygen is forcibly supplied from the atmosphere duct 18 to the exhaust gas chamber 17. Thereafter, when it comes time to terminate the negative voltage control, the switch circuit 64 is switched from the s2-connection state to the s1-connection state, to thereby switch from the negative voltage control to the normal control.

According to the fourth embodiment described above, it is possible to suppress the delay of the sensor activation due to the rich drift at the time of the start of sensor operation, like in the foregoing embodiments. Hence, according to the fourth embodiment, it is possible that the element current IL early reaches a normal level, and accordingly the activation of the A/F sensor can be determined early.

Fifth Embodiment

Figure 16A:
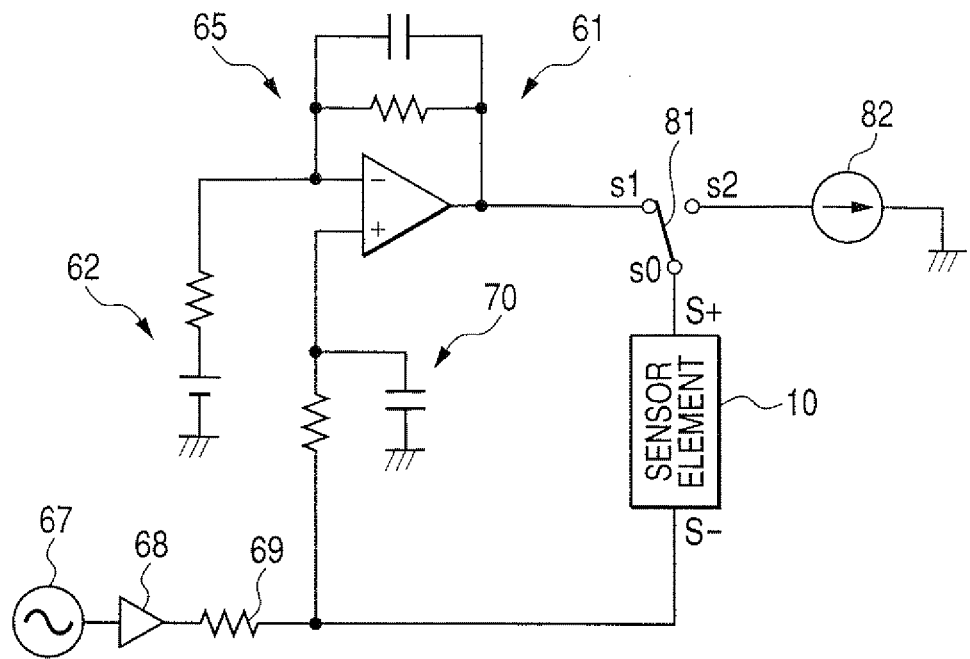
FIG. 16A is a circuit diagram of a sensor control circuit of a gas sensor control apparatus according to a fifth embodiment of the invention.
Figure 16B:
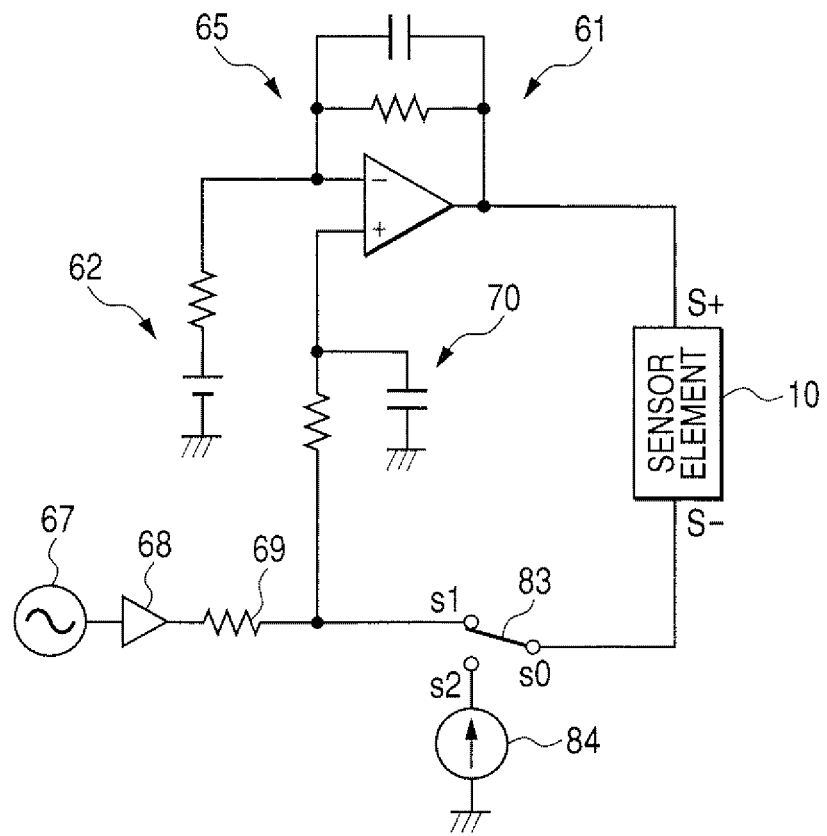
FIG. 16B is a circuit diagram of a modification of the sensor control circuit shown in FIG. 16A.

Next, a gas sensor control apparatus according to a fifth embodiment of the invention is described. The fifth embodiment differs from the fourth embodiment in that the sensor control circuit is provided with a constant current circuit used to supply oxygen from the atmosphere duct 18 to the exhaust gas chamber 17. FIG. 16A is a circuit diagram of the sensor control circuit of the gas sensor control apparatus according to the fifth embodiment, and FIG. 16B is a circuit diagram of the sensor control circuit of a modification of the gas sensor control circuit shown in FIG. 16A. In FIGS. 16A and 16B, the same reference characters as those in FIG. 15 indicate the same or corresponding components shown in FIG. 15, and some of the components common to the fourth and fifth embodiments (the microcomputer 78, for example) are omitted from being shown.

As shown in FIG. 16A, the positive terminal (S+ terminal) of the sensor element 10 is connected with a switch circuit 81. The switch circuit 81 is switched in accordance with a switch command signal from the microcomputer (omitted from being shown). Normally, the switch circuit 81 is switched in the s1-connection state in order to perform the normal control on the A/F sensor. When the switch circuit 81 is switched in the s2-connection state, the positive terminal (S+ terminal) of the sensor element is connected to a constant current circuit 82. By the operation of the constant current circuit 82, which is a current drawing type circuit, the negative current In flows in the direction from the exhaust-gas side electrode 15 (S−) to the atmosphere-side electrode 16 (S+).

As shown in FIG. 16B, the modification of the sensor control circuit shown in FIG. 16A includes a switch circuit 83 and a constant current circuit 84 instead of the switch circuit 81 and the constant current circuit 82. By the operation of the constant current circuit 84, which is a current discharge type circuit, the negative current In flows in the direction from the exhaust-gas side electrode 15 (S−) to the atmosphere-side electrode 16 (S+).

As shown in FIGS. 16A and 16B, with the start of sensor operation, the switch circuit 81 (or 83) is switched in the s-2 connection state, as a result of which the negative current In flows through the sensor element 10 by the operation of the constant current circuit 82 (or 84). As a result, oxygen is forcibly supplied from the atmosphere duct 18 to the exhaust gas chamber 17. Thereafter, when it comes time to terminate the negative voltage control, the switch circuit 81 (or 83) is switched from the s2-connection state to the s1-connection state, to thereby switch from the negative voltage control to the normal control.

According to the fifth embodiment described above, it is possible to suppress the delay of the sensor activation due to the rich drift at the time of the start of sensor operation, like in the foregoing embodiments. Hence, according to the fifth embodiment, it is possible that the element current IL reaches a normal level early, and accordingly the activation of the A/F sensor can be determined early.

Sixth Embodiment

The above embodiments have been described as controlling the A/F sensor including the sensor element having the structure shown in FIG. 2, however, the present invention is applicable to a sensor element having a structure different from that shown in FIG. 2. For example, the A/F sensor may include, instead of the 1-cell type sensor element as shown in FIG. 2, a 2-cell type sensor element having a pump cell and an electromotive force cell. In other words, the sensor element may have a structure including two or more solid electrolyte layers, instead of the structure including only one solid electrolyte layer. Furthermore, the present invention is applicable to a gas sensor including a sensor element having not the lamination-type structure, but a cup-type structure.

In the following, two examples of a 2-cell type sensor element are explained with reference to FIG. 17A and FIG. 17B.

Figure 17A:
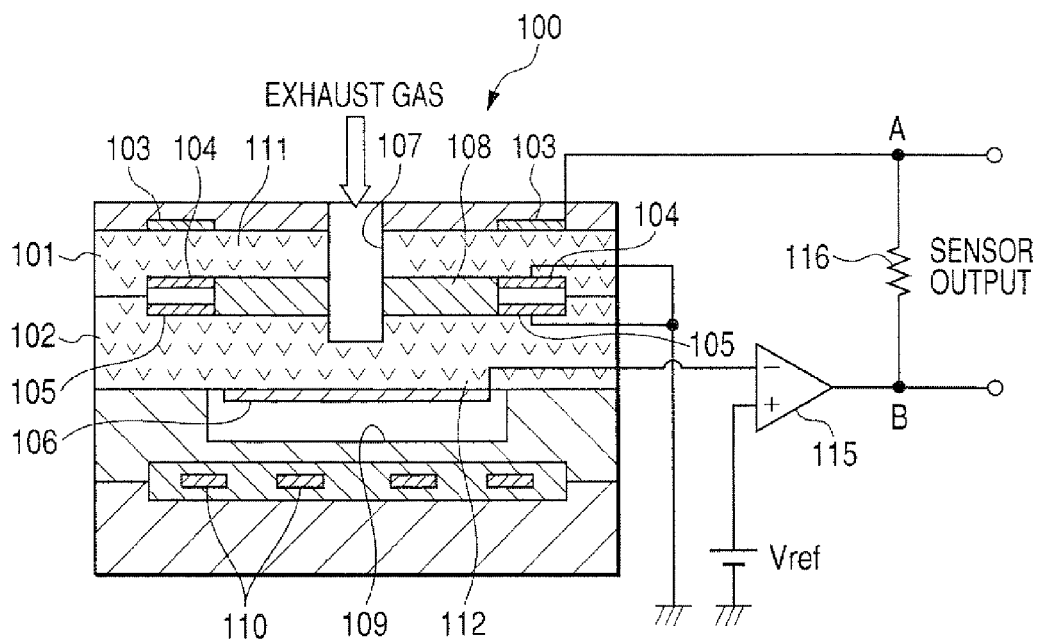
FIGS. 17A and 17B are cross-sectional views of gas sensors controlled by a gas sensor control apparatus according to a sixth embodiment of the invention.

The sensor element 100 shown in FIG. 17A includes two solid electrolyte layers 101 and 102. The solid electrolyte layer 101 is provided with a pair of electrodes 103 and 104 located on the opposite sides thereof. The solid electrolyte layer 102 is provided with a pair of electrodes 105 and 106 located on the opposite sides thereof. Although each of the electrodes 103 to 105 is shown as having two parts located at different positions, they are connected to each other and constitute a single electrode.

The solid electrolyte layer 101 and the electrodes 103, 104 constitute a pump cell 111. The solid electrolyte layer 102 and the electrodes 105, 106 constitute an oxygen detection cell 112. Like the foregoing sensor element 10, the sensor element 100 has a laminated structure. The reference numeral 107 denotes a gas introducing hole, 108 denotes a porous diffusion layer, 109 denotes an atmosphere duct, and 110 denotes a heater. The electrode 104 on the side of the porous diffusion layer 108 serves as a gas detecting electrode, and the electrode 103 serves as a reference electrode.

The voltage of the electrode 106 of the oxygen detection cell 112 is inputted to the negative input terminal of a comparator 115, and a reference voltage Vref is inputted to a positive input terminal of the comparator 115. Between the electrode 103 of the pump cell 111 and the output terminal of the comparator 115, a current measuring resistor 116 is connected. The voltage across both ends (the point A and point B) of the current measuring resistor 116 is taken out as a sensor output.

The oxygen detection cell 112 generates a binary electromotive force output (0 V or 0.9 V) depending on whether exhaust gas is lean or rich with respect to the stoichiometric point. When the exhaust gas is lean, the electromotive force output of the oxygen detection cell 112 is low (0 V), and accordingly, the output (the voltage of the point B, referred to as the "B-point voltage" hereinafter) of the comparator 115 is at a high level. Accordingly, when the exhaust gas is lean, a current flows through the current measuring resistor 116 in the direction of from the point B to the point A. On the other hand, when the exhaust gas is rich, the electromotive force output of the oxygen detection cell 112 is high (0.9 V), and accordingly, the output of the comparator 115 is at a low level. Accordingly, when the exhaust gas is rich, a current flows through the current measuring resistor 116 in the direction of from the point A to the point B. The oxygen detection cell 112 is also referred to as an electromotive force cell, or an oxygen concentration detection cell.

Figure 17B:
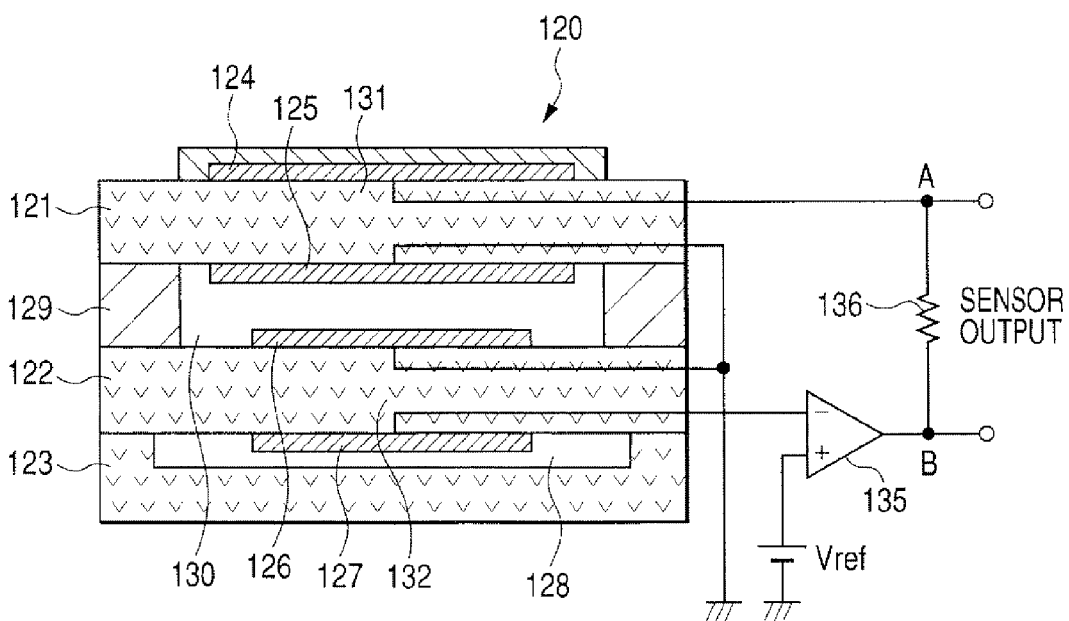

The sensor element 120 shown in FIG. 17B includes three solid electrolyte layers 121, 122 and 123. The solid electrolyte layer 121 is provided with a pair of electrodes 124 and 125 located on the opposite sides thereof. The solid electrolyte layer 122 is provided with a pair of electrodes 126 and 127 located on the opposite sides thereof.

The solid electrolyte layer 121 and the electrodes 124, 125 constitute a pump cell 131. The solid electrolyte layer 122 and the electrodes 126, 127 constitute a oxygen detection cell 132. The solid electrolyte layer 123 forms a wall member of an oxygen reference chamber 128. Like the foregoing sensor element 10, the sensor element 120 has a laminated structure. The reference numeral 129 denotes a porous diffusion layer, and 130 denotes a gas detection chamber (exhaust gas chamber). The electrode 125 on the side of the gas detection chamber 130 serves as a gas detecting electrode, and the electrode 124 serves as a reference electrode.

The voltage of the electrode 127 of the oxygen detection cell 132 is inputted to the negative input terminal of a comparator 135, and the reference voltage Vref is inputted to the positive input terminal of the comparator 115. Between the electrode 124 of the pump cell 131 and the output terminal of the comparator 135, a current measuring resistor 136 is connected. The voltage across both ends (the point A and point B) of the current measuring resistor 136 is taken out as a sensor output. When exhaust gas is lean, a current flows through the current measuring resistor 136 in the direction from the point B to the point A. On the other hand, when the exhaust gas is rich, a current flows through the current measuring resistor 136 in the direction from the point A to the point B.

Next, the structure of a sensor control circuit of a gas sensor control apparatus for controlling the gas sensor including the 2-cell type sensor element as explained above with reference to FIG. 17A is described with reference to FIG. 18.

Figure 18:
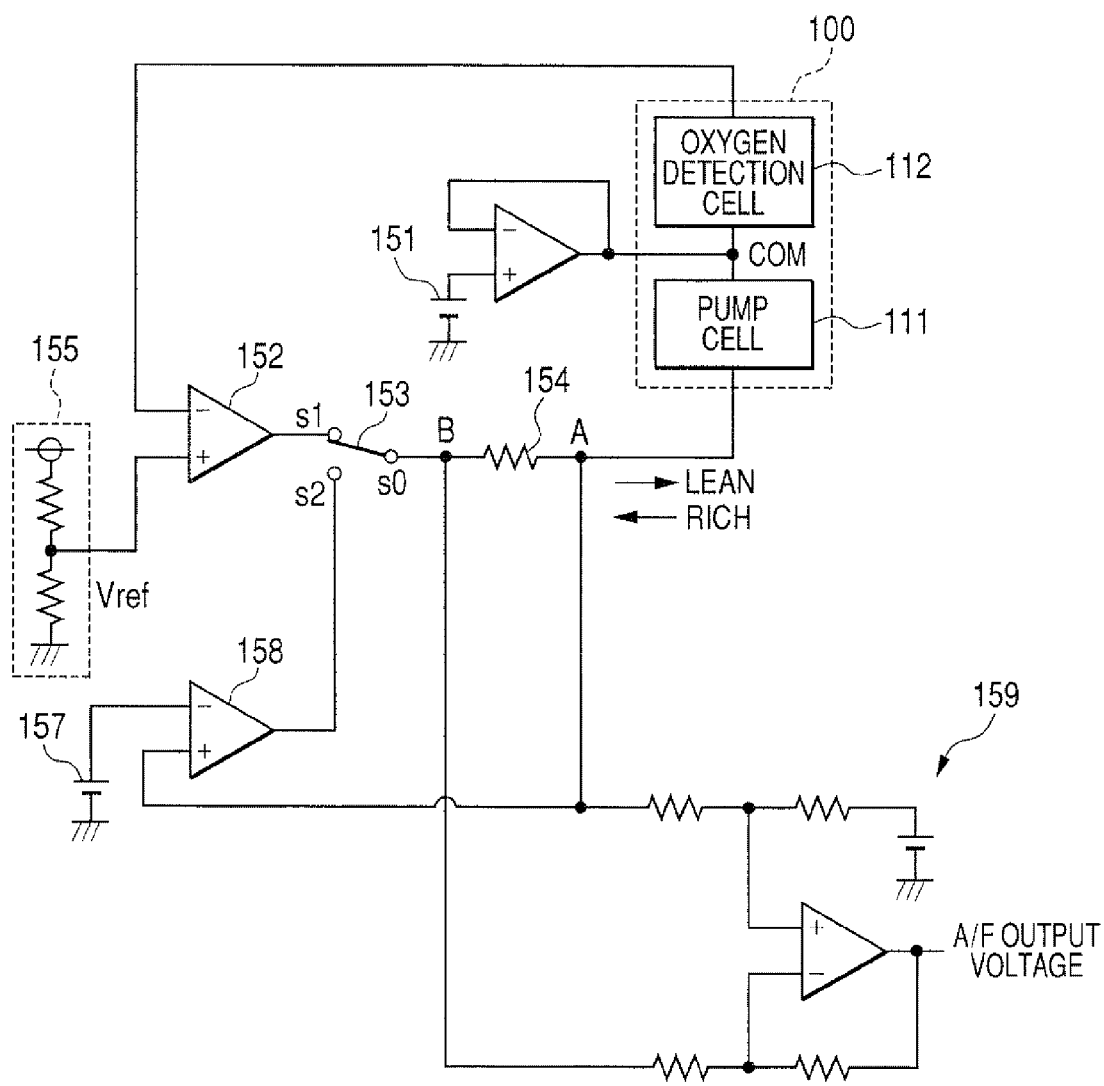
FIG. 18 is a circuit diagram of a sensor control circuit of the gas sensor control apparatus for controlling the gas sensor shown in FIG. 17A.

As shown in FIG. 18, a common terminal COM of the pump cell 111 and the oxygen detection cell 112 is connected to a reference voltage source 151 of the sensor control circuit. The voltage of the common terminal COM is fixed at the same voltage as the reference voltage source 151, which is set to 2.5 V, for example. The pump cell 111 and the oxygen detection cell 112 are further connected with a series circuit of an operational amplifier 152, a switch circuit 153, and a current measuring resistor 154. The non-inverting input terminal of the operational amplifier 152 is connected with a comparison voltage generation circuit 155 which generates a comparison voltage Vref (0.45 V). When exhaust gas is lean, a current flows through the current measuring resistor 154 in the direction from the point B to the point A. On the other hand, when the exhaust gas is rich, a current flows from the point A to the point B. The pump cell 111 is feedback-controlled so that the output voltage of the oxygen detection cell 112 is kept at a certain value. Since such feedback control is well known, any specific feedback control circuit is not shown, and an explanation thereof is omitted here.

Both ends (the point A and the point B) of the current measuring resistor 154 are connected respectively to the non-inverting input terminal and the inverting input terminal of a differential amplifier circuit 159. The output of the differential amplifier circuit 159 is supplied to the microcomputer (not shown) as an A/F output voltage.

The switch circuit 153 is switched in accordance with a switch command signal from the microcomputer (omitted from being shown). Normally, the switch circuit 153 is switched in the s1-connection state in order to perform the normal control on the A/F sensor. In this state, the element current flowing through the pump cell 111 is feedback-controlled on the basis of the electromotive force signal of the oxygen detection cell 112. On the other hand, when the switch circuit 153 is in the s2-connection state, the output terminal of the operational amplifier 158 is connected to one end (the point B) of the current measuring resistor 154. The inverting input terminal and the non-inverting input terminal of the operational amplifier 158 are connected respectively to a voltage source 157 and the other end (the point A) of the current measuring resistor 154. The voltage of the voltage source 157 is set to 3.5 V, for example.

At the time of the start of sensor operation with the start of an engine (at the time of the start of power supply to the heater), the switch circuit 153 is switched in the s2-connection state. At this time, if the engine is cold-started, the voltage of the common terminal COM and the voltage of the point A both become 2.5V. As a result, the inverting input terminal and the non-inverting input terminal of the operational amplifier 158 are applied with 3.5 V and 2.5 V, respectively. In consequence, a current flows from the electrode 104 (gas detecting electrode) to the electrode 103 (reference electrode), causing oxygen ions to move from the electrode 103 to the electrode 104. Accordingly, since oxygen is forcibly supplied to the electrode 104, moisture or organic matter present on the side of the electrode 104 at the time of the start of sensor operation can be removed. Thereafter, when it comes time to terminate the negative voltage control, the switch circuit 153 is switched from the s2-connection state to the s1-connection state, to thereby switch from the negative voltage control to the normal control.

Figure 19:
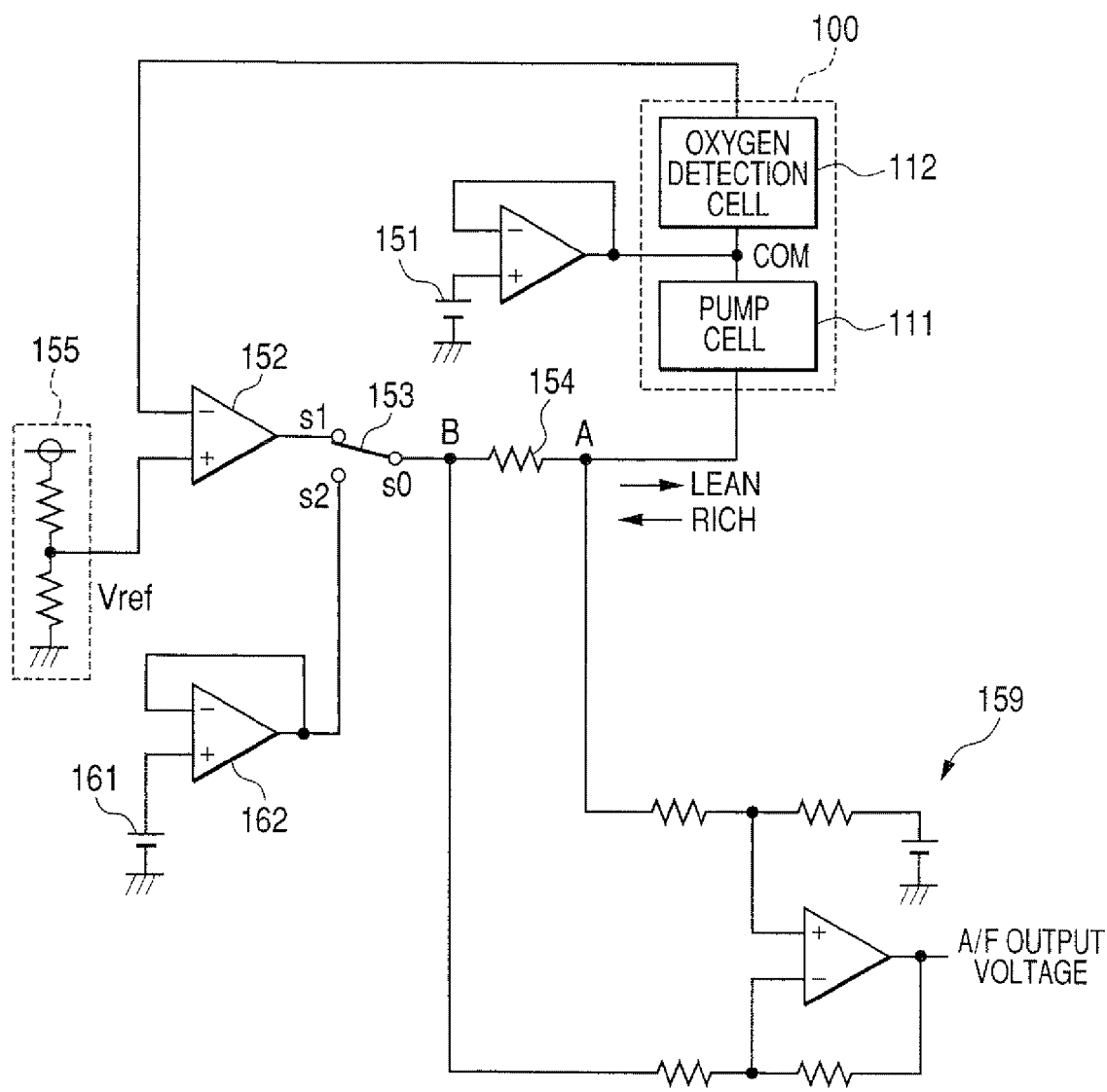
FIGS. 19, 20A, 20B, 21, 22, 23A and 23B are circuit diagrams of modifications of the sensor control circuit shown in FIG. 18.

FIG. 19 is a circuit diagram of a modification of the sensor control circuit shown in FIG. 18. The sensor control circuit shown in FIG. 19 differs from the sensor control circuit shown in FIG. 18 in that the inverting input terminal of an operational amplifier 162, which is connected to the stationary contact s2 of the switch circuit 153, is connected to the output terminal of the operational amplifier 162, and the non-inverting input terminal of the operational amplifier 162 is connected to a voltage source 161. In the sensor control circuit shown in FIG. 19, by switching the switch circuit 153 in the s2-connection state, the B-point voltage can be kept at the same voltage as the voltage source 162 (1.5 V, for example).

At the time of the start of sensor operation with the start of the engine, the switch circuit 153 is switched in the s-2 connection state. As a result, the voltage of the common terminal COM and the B-point voltage become 2.5 V, and 1.5 V, respectively. In consequence, a current flows from the electrode 104 (gas detecting electrode) to the electrode 103 (reference electrode), causing oxygen ions to move from the electrode 103 to the electrode 104. Accordingly, since oxygen is forcibly supplied to the electrode 104, moisture or organic matter present on the side of the electrode 104 at the time of the start of sensor operation can be removed. Thereafter, when it comes time to terminate the negative voltage control, the switch circuit 153 is switched from the s2-connection state to the s1-connection state, to thereby switch from the negative voltage control to the normal control.

According to the sensor control circuits shown in FIG. 18 and FIG. 19, it is possible to suppress the delay of the sensor activation due to the rich drift at the time of the start of sensor operation, like in the foregoing embodiments. Hence, according to these sensor control circuits shown in FIG. 18 and FIG. 19, it is possible that the element current IL early reaches a normal level, and accordingly the activation of the A/F sensor can be determined early.

Figure 20A:
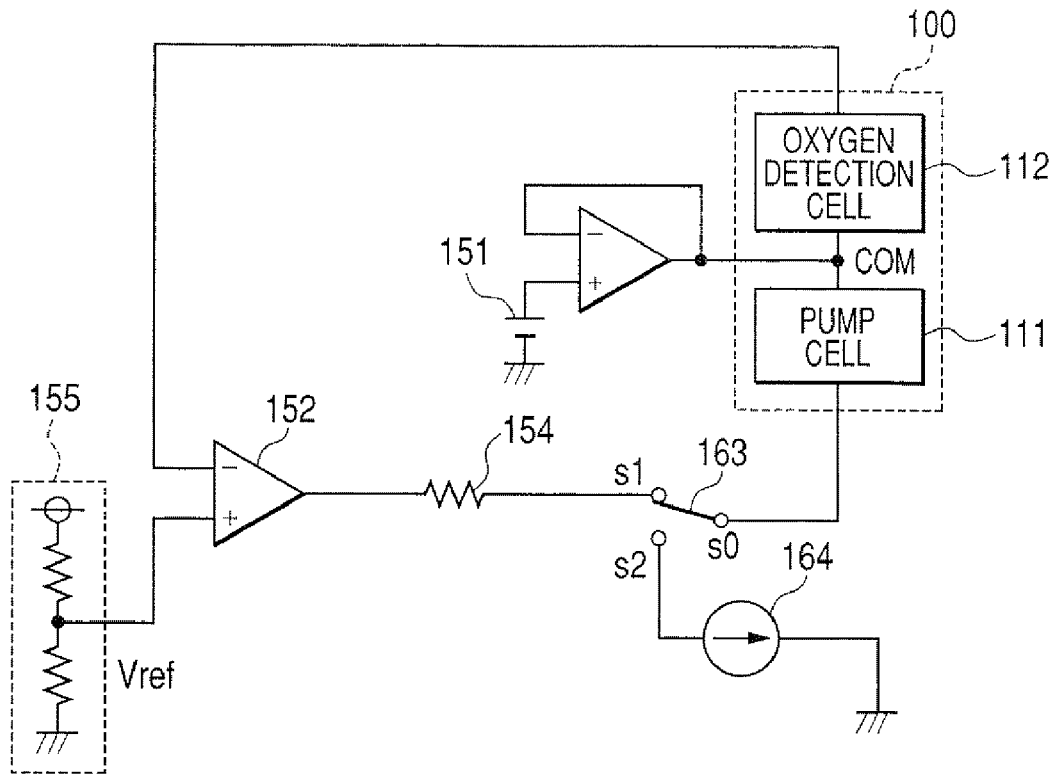
Figure 20B:
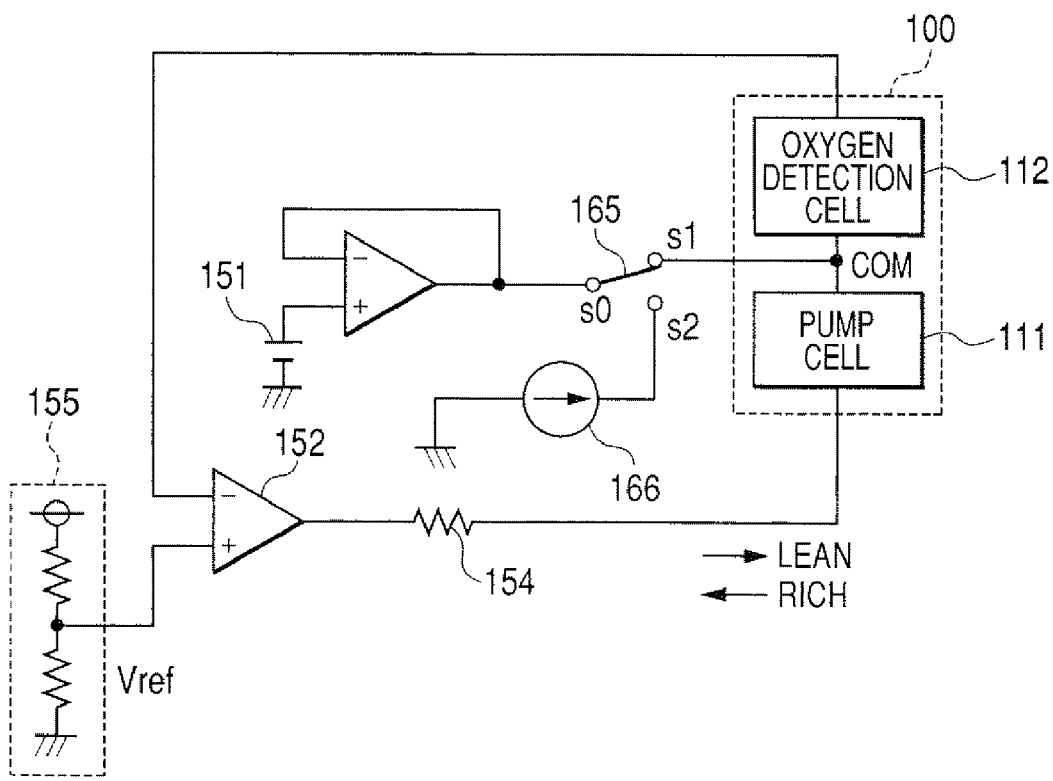

FIG. 20A and FIG. 20B shows further modifications of the sensor control circuit shown in FIG. 18. In FIG. 20A and FIG. 20B, the differential amplifier 159 and some other components are omitted from being shown for simplifying the drawings.

In the sensor control circuit shown in FIG. 20A, the movable contact s0 of a switch circuit 163 is connected to one of the two terminals of the pump cell 111, which is on the side opposite to the common terminal COM (that is, on the side of the electrode 103 as a reference electrode). The switch circuit 163 is switched in accordance with a switch command signal from the microcomputer (omitted from being shown). Normally, the switch circuit 163 is switched in the s1-connection state, in order to perform the normal control on the A/F sensor.

On the other hand, when the switch circuit 163 is switched in the s2-connection state, a constant current circuit 164 is connected to the terminal of the pump cell 111 which is on the side of the electrode 103 as a reference electrode. By the operation of the constant current circuit 164, which is a current drawing type circuit, a current flows in the direction from the electrode 104 to the electrode 103 (in the same direction as the direction when the exhaust gas is rich). As a result, since oxygen is forcibly supplied to the electrode 104, moisture or organic matter present on the side of the electrode 104 at the time of the start of sensor operation can be removed.

The sensor control circuit shown in FIG. 20B differs from the sensor control circuit shown in FIG. 20A in that, instead of the switch circuit 163 and the constant current circuit 164, a switch circuit 165 and a constant current circuit 166 are provided on the side of the common terminal COM (on the side of the electrode 104) of the pump cell 111. By the operation of the constant current circuit 166, which is a current discharge type circuit, a current flows in the direction from the electrode 104 to the electrode 103 (in the same direction as the direction when the exhaust gas is rich). As a result, since oxygen is forcibly supplied to the electrode 104, moisture or organic matter present on the side of the electrode 104 at the time of the start of sensor operation can be removed.

Figure 21:
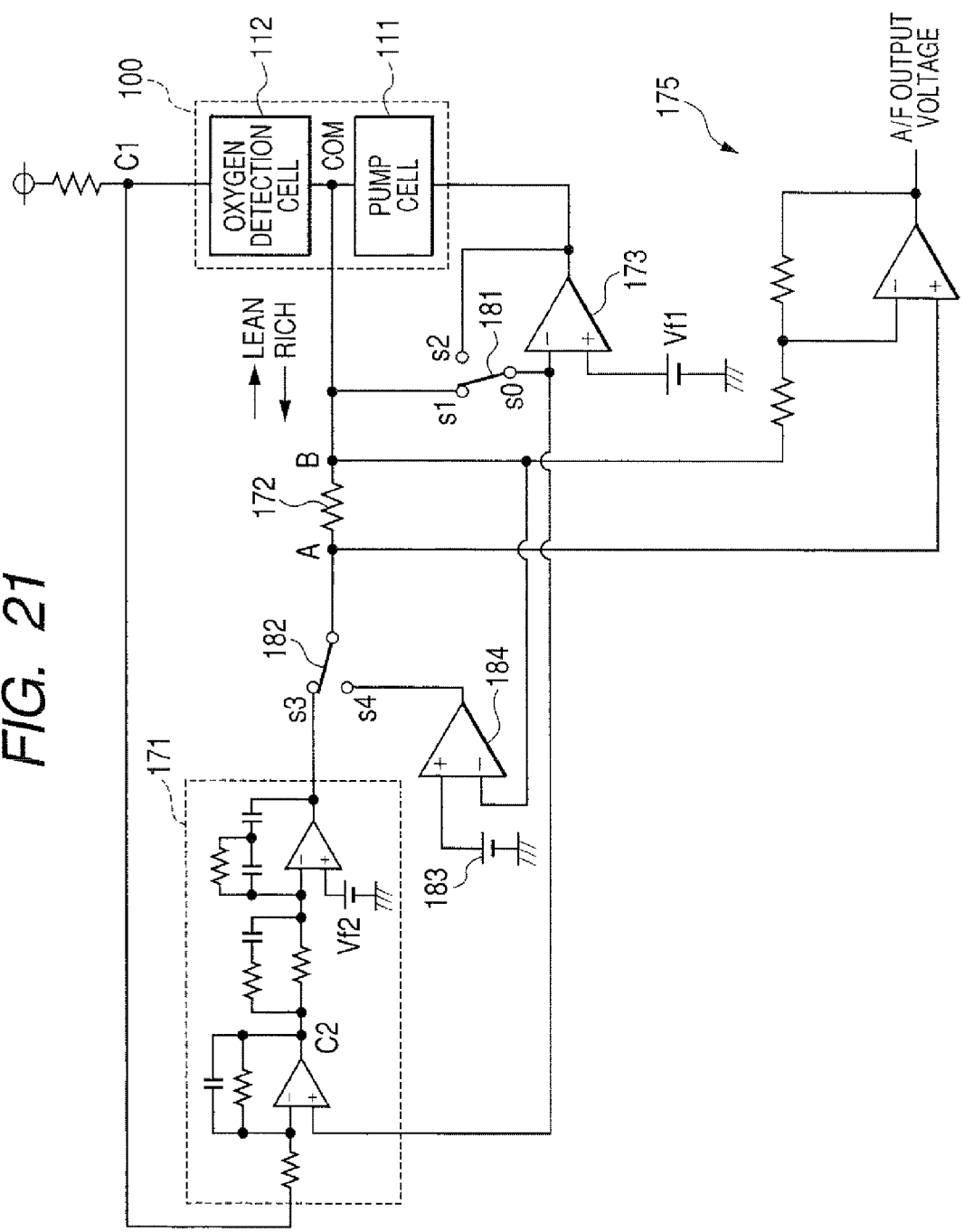

FIG. 21 is a circuit diagram of a sensor control circuit of a further modification of the sensor control circuit shown in FIG. 18.

In the sensor control circuit shown in FIG. 21, the common terminal COM of the pump cell 111 and the oxygen detection cell 112 is applied with the same voltage as the reference voltage Vref (3 V, for example) through an operational amplifier 173 and a switch circuit 181. When the switch circuit 181 is switched in the s1-connection state, the voltage of the point B (the voltage of the common terminal COM) is fixed at 3 V. The oxygen detection cell 112 is connected with a series circuit of a feedback circuit 171, a switch circuit 182, and a current measuring resistor 172. A reference voltage Vf2 in the feedback circuit 171 is set to 2.55 V, for example.

In the following, the operation of the sensor control circuit shown in FIG. 21 when exhaust gas is rich is explained. When the exhaust gas is rich, since the voltage of a point C in FIG. 21 is as high as 3.45 V by the electromotive force of the oxygen detection cell 112, the voltage of a point C2 in the feedback circuit 171 is at a low level. In consequence, the output of the feedback circuit 171, that is the voltage of the point A rises to a high level. Hence, when the exhaust gas is rich, a current flows through the current measuring resistor 172 in the direction from the point A to the point B. On the other hand, when the exhaust gas is lean, a current flows through the current measuring resistor 172 in the direction from the point B to the point A.

Both ends (the point A and the point B) of the current measuring resistor 172 are connected respectively to the non-inverting input terminal and the inverting input terminal of an amplifier circuit 175. The output of the amplifier circuit 175 is supplied to the microcomputer (omitted from being shown) as an A/F output voltage.

The switch circuits 181 and 182 are switched in accordance with a switch command signal from the microcomputer (omitted from being shown). Normally, the switch circuit 181 is switched in the s1-connection state, and the switch circuit 182 is switched in the s3-connection state, in order to perform the normal control on the A/F sensor. In this state, the element current flowing through the pump cell 111 is feedback-controlled on the basis of the electromotive force signal of the oxygen detection cell 112.

On the other hand, when the switch circuit 182 is switched in the s2-connection state, the inverting input terminal and the output terminal of the operational amplifier 173 are connected to each other. As a result, the voltage at one of the two terminals of the pump cell 111, which is on the side opposite to the common terminal COM (that is, on the side of the electrode 103 as a reference electrode) becomes 3.0 V. Further, when the switch circuit 182 is switched in the s4-connection state, the output terminal of an operational amplifier 184 is connected to one end (the point A) of the current measuring resistor 172. The non-inverting input terminal and the inverting input terminal of the operational amplifier 184 are connected respectively to a voltage source 183, and the other end (the point B) of the current measuring resistor 172. By switching the switch circuit 182 in the s4-connection state, the voltage at the point B can be kept at the same voltage as the voltage source 182 (4.0 V, for example).

At the time of the start of sensor operation with the start of the engine, the switch circuit 181 is switched in the s2-connection state, and the switch circuit 182 is switched in the s4-connection state. As a result, the voltage of one terminal of the pump cell 111 on the side of the common terminal COM becomes 4.0 V, and the other terminal on the side opposite to the common terminal COM becomes 3.0 V. In consequence, a current flows from the electrode 104 (gas detecting electrode) to the electrode 103 (reference electrode), causing oxygen ions to move from the electrode 103 to the electrode 104. As a result, since oxygen is forcibly supplied to the electrode 104, moisture or organic matter present on the side of the electrode 104 at the time of the start of sensor operation can be removed. Thereafter, when it comes time to terminate the negative voltage control, the switch circuit 181 is switched from the s2-connection state to the s1-connection state, and the switch circuit 182 is switched from the S4-connection state to the s3-connection state, to thereby switch from the negative voltage control to the normal control.

Figure 22:
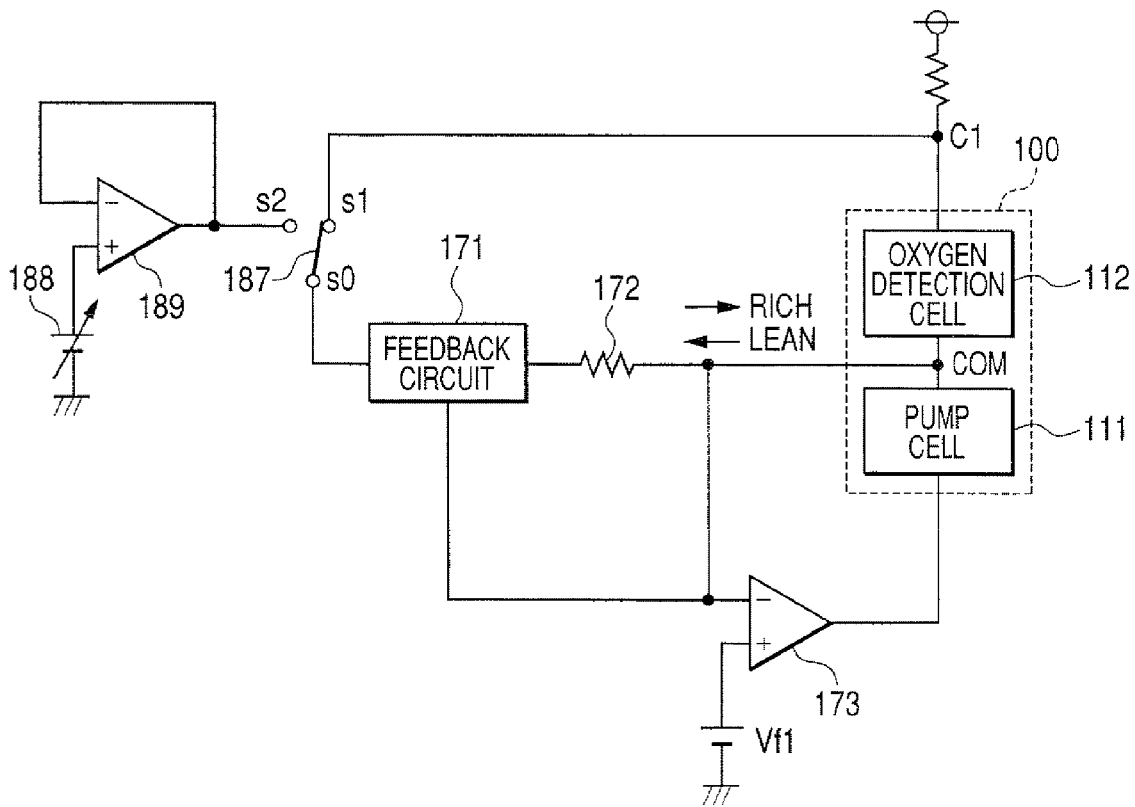

FIG. 22 is a circuit diagram showing a modification of the sensor control circuit shown in FIG. 21. The sensor control circuit shown in FIG. 22 differs from the sensor control circuit shown in FIG. 21 in that the switch circuits 181, 182 and some other components are removed, and instead, a switch circuit 187 is provided between the oxygen detection cell 112 and the feedback circuit 171. When the switch circuit 187 is switched in the s2-connection state, the voltage of a voltage source 188 is inputted to the feedback circuit 171 through an operational amplifier 189. The voltage of the voltage source 188 can be variably set within a range of 3.45 V to 3.9 V. In this sensor control circuit, the switch circuit 187 is switched in the s2-connection state at the time of the start of sensor operation, as a result of which a voltage equivalent to the voltage in the case where the exhaust gas is rich is forcibly inputted to the feedback circuit 171.

According to any of the sensor control circuits shown in FIG. 21 and FIG. 22, it is possible to suppress the delay of the sensor activation due to the rich drift at the time of the start of sensor operation, like in the foregoing embodiments. Hence, according to these sensor control circuits, it is possible that the element current IL early reaches a normal level, and accordingly the activation of the A/F sensor can be determined early.

Figure 23A:
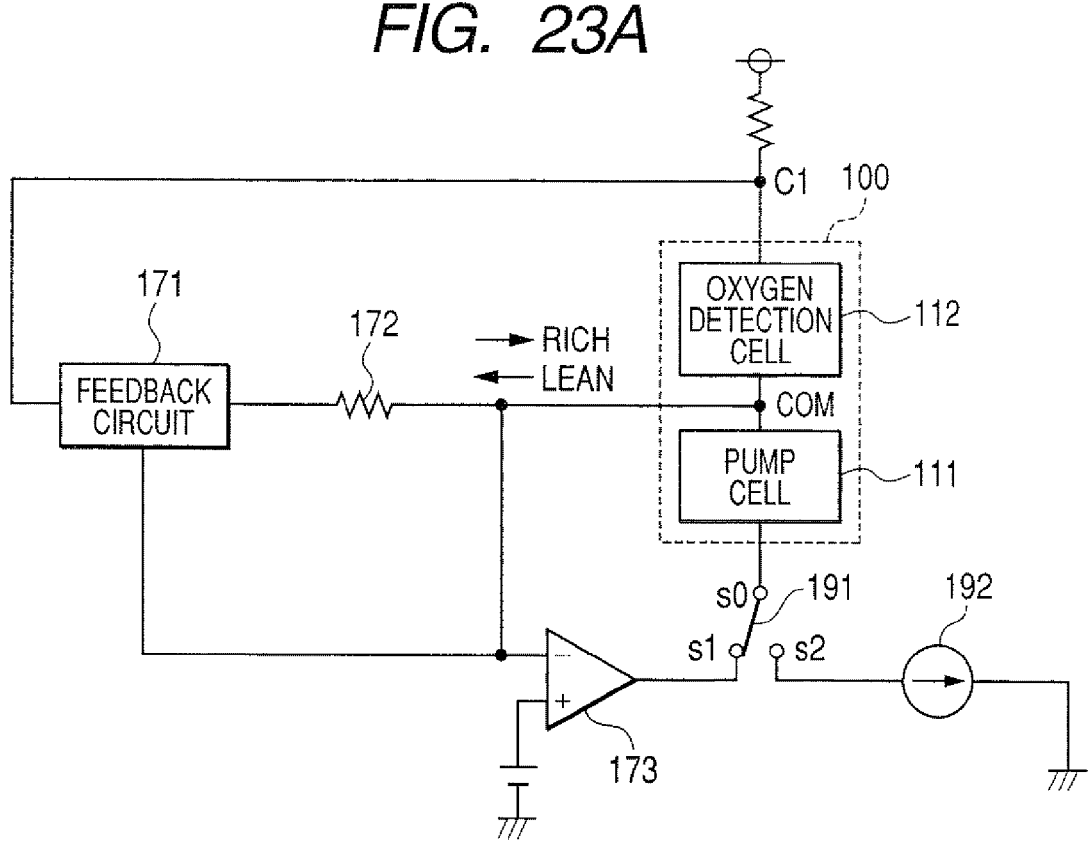
Figure 23B:
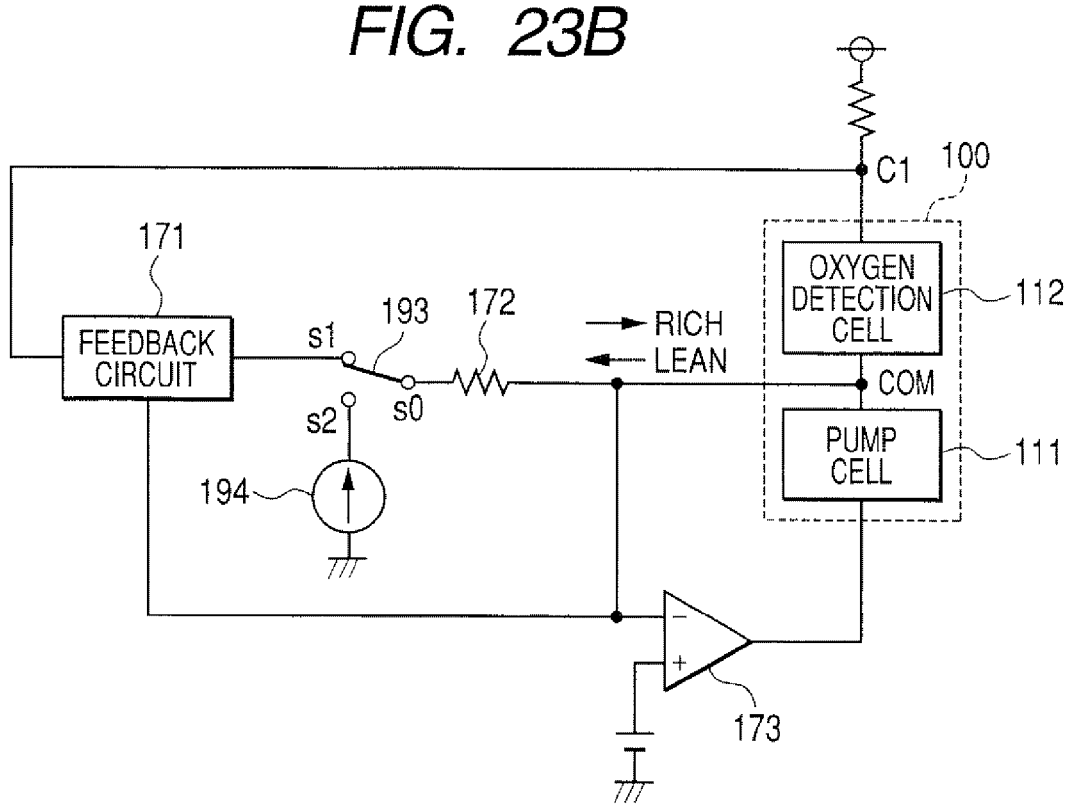

The sensor control circuit shown in FIG. 21 may be further modified as shown in FIG. 23A or FIG. 23B.

In the sensor control circuit shown in FIG. 23A, the movable contact s0 of a switch circuit 191 is connected to one of the two terminals of the pump cell 111, which is on the side opposite to the common terminal COM (that is, on the side of the electrode 103 as a reference electrode). The switch circuit 191 is switched in accordance with a switch command signal from the microcomputer (omitted from being shown). Normally, the switch circuit 191 is switched in the s1-connection state in order to perform the normal control on the A/F sensor.

On the other hand, when the switch circuit 191 is switched in the s2-connection state, a constant current circuit 192 is connected to the terminal of the pump cell 111 which is on the side of the electrode 103 as a reference electrode. By the operation of the constant current circuit 192, which is a current drawing type circuit, a current flows in the direction from the electrode 104 to the electrode 103 (in the same direction as the direction when the exhaust gas is rich). As a result, since oxygen is forcibly supplied to the electrode 104, moisture or organic matter present on the side of the electrode 104 at the time of the start of sensor operation can be removed.

The sensor control circuit shown in FIG. 23B differs from the sensor control circuit shown in FIG. 23A in that instead of the switch circuit 191 and the constant current circuit 192, a switch circuit 193 and a constant current circuit 194 are provided between the feedback circuit 171 and the current measuring resistor 172 on the side of the common terminal COM (on the side of the electrode 104) of the pump cell 111. By the operation of the constant current circuit 194, which is a current discharge type circuit, a current flows in the direction from the electrode 104 to the electrode 103 (in the same direction as the direction when the exhaust gas is rich). As a result, since oxygen is forcibly supplied to the electrode 104, moisture or organic matter present on the side of the electrode 104 at the time of start of sensor operation can be removed.

It is matter of course that various modifications can be made to the above embodiments as described below.

The present invention is applicable to a gas sensor control apparatus for controlling a gas sensor other than the A/F sensor or $O_2$ sensor. For example, the present invention is applicable to a Nox sensor for measuring NOx concentration. The NOx sensor may be a composite-type gas sensor including a plurality of cells formed by solid electrolyte layers, a first one of the cells serving as a pump cell for removing or pumping out oxygen from a gas under measurement and measuring oxygen concentration in the gas, a second one of the cells serving as a sensor cell for measuring concentration of a specific gas component in the gas from which oxygen has been removed. The NOx sensor may further include a third cell serving as a monitor cell or a second pump cell for measuring concentration of remaining oxygen in the gas.

The present invention is also applicable to a gas sensor control apparatus for controlling a gas sensor for measuring HC concentration or CO concentration. The gas sensor may be configured to remove surplus oxygen from a gas under measurement, decompose HC or CO from the gas from which the surplus oxygen has been removed to measure concentration of HC or CO.

The present invention is applicable to a gas sensor control apparatus for controlling a gas sensor located in an air intake pipe of a gasoline engine. The present invention is also applicable to a gas sensor control apparatus not only for gasoline engines, but other types of engines, for example, diesel engines. The present invention may be applied to a gas sensor control apparatus used for other than vehicle engines.

The above explained preferred embodiments are exemplary of the invention of the present application which is described solely by the claims appended below. It should be understood that modifications of the preferred embodiments may be made as would occur to one of skill in the art.

What is claimed is:

1. A gas sensor control apparatus for controlling a gas sensor including a sensor element having a solid electrolyte layer, and first and second electrodes located on opposite sides of said solid electrolyte layer, said first electrode serving as a gas detecting electrode, said second electrode serving as a reference electrode, said sensor element generating, as a sensor output, a current flowing between said first and second electrodes having a value depending on concentration of a specific gas component contained in a gas under measurement, said gas sensor control apparatus being configured to:
   determine whether or not it is time for said gas sensor to start operation; and
   control a forced supply of oxygen from a side of said second electrode to a side of said first electrode on a temporary basis when a determination result of whether or not it is time for the gas sensor to start operation becomes affirmative;
   wherein said control is configured to measure an impedance of said sensor element, said control is configured to stop forcibly supplying oxygen to the side of said first electrode when said measured impedance has reached a predetermined value, and the impedance of said sensor element is an AC impedance obtained by temporarily changing a voltage applied to the sensor element to an alternating voltage.

2. The gas sensor control apparatus according to claim 1, wherein:
   said gas sensor includes an electrical heater for heating said sensor element, and
   said gas sensor control apparatus is further configured to start power supply to said electrical heater when said determination of whether or not it is time for the gas sensor to start operation becomes affirmative.

3. The gas sensor control apparatus according to claim 2, wherein said control applies an oxygen supply voltage between said first and second electrodes with said first electrode being positive in voltage, and said second electrode being negative in voltage, in order to supply oxygen from the side of said second electrode to the side of said first electrode.

4. The gas sensor control apparatus according to claim 3, wherein said control varies said oxygen supply voltage after said gas sensor starts operation.

5. The gas sensor control apparatus according to claim 4, wherein said control gradually decreases said oxygen supply voltage in accordance with an expected variation with time of a DC impedance of said sensor element.

6. The gas sensor control apparatus according to claim 3, wherein said control includes a first voltage application including applying a gas detection voltage between said first and second electrodes for detecting concentration of said specific gas component, and a second voltage application including applying said oxygen supply voltage between said first and second electrodes, said control being configured to cause said second voltage application to apply said oxygen supply voltage between said first and second electrodes for a certain time period immediately after starting power supply to said electrical heater, and thereafter cause said first voltage application apply said gas detection voltage between said first and second electrodes.

7. The gas sensor control apparatus according to claim 6, wherein said second voltage application is configured to apply a predetermined constant voltage between said first and second electrodes as said oxygen supply voltage, said control being configured to apply a voltage intermediate between said oxygen supply voltage and said gas detection voltage during a transition period in which said second voltage application is switched to said first voltage application.

8. The gas sensor control apparatus according to claim 1, wherein said control is configured to forcibly flow a current from said first electrode to said second electrode to forcibly supply oxygen from the side of said second electrode to the side of said first electrode.

9. The gas sensor control apparatus according to claim 8, wherein said control includes passing a constant current in a direction from said first electrode to said second electrode to supply oxygen from the side of said second electrode to the side of said first electrode.

10. The gas sensor control apparatus according to claim 1, wherein said control includes calculating an integration value of said sensor output integrated from a time when said gas sensor starts operation, said as sensor control apparatus being further configured to stop forcibly supplying oxygen to the side of said first electrode when said integration value has reached a predetermined value.

11. The gas sensor control apparatus according to claim 1, wherein said control includes calculating a value of integrated electric power supplied to an electrical heater of the gas sensor, said gas sensor control apparatus being further configured to stop forcibly supplying oxygen to the side of said first electrode when said integrated electric power has reached a predetermined value.

12. The gas sensor control apparatus according to claim 1, wherein said gas sensor is mounted on an exhaust passage of an internal combustion engine, and said gas under measurement is an exhaust gas flowing through said exhaust passage.

13. A method of controlling a gas sensor including a sensor element having a solid electrolyte layer, and first and second electrodes located on opposite sides of said solid electrolyte layer, said first electrode serving as a gas detecting electrode, said second electrode serving as a reference electrode, said sensor element generating, as a sensor output, a current flowing between said first and second electrodes having a value depending on concentration of a specific gas component contained in a gas under measurement, said method comprising:
   determining whether or not it is time for said gas sensor to start operation;

controlling a forced supply of oxygen from a side of said second electrode to a side of said first electrode on a temporary basis when a determination result of whether or not it is time for the gas sensor to start operation becomes affirmative; and measuring an impedance of said sensor element;

wherein said controlling includes stopping forced supplying of oxygen to the side of said first electrode when said measured impedance has reached a predetermined value, and the impedance of said sensor element is an AC impedance obtained by temporarily changing a voltage applied to the sensor element to an alternating voltage.

14. The method according to claim 13, wherein:

said gas sensor includes an electrical heater for heating said sensor element, and said method further comprises starting power supply to said electrical heater when said determination of whether or not it is time for the gas sensor to start operation becomes affirmative.

15. The method according to claim 14, wherein said controlling includes applying an oxygen supply voltage between said first and second electrodes with said first electrode being positive in voltage, and said second electrode being negative in voltage, in order to supply oxygen from the side of said second electrode to the side of said first electrode.

16. The method according to claim 15, wherein said controlling includes varying said oxygen supply voltage after said gas sensor starts operation.

17. The method according to claim 16, wherein said controlling includes gradually decreasing said oxygen supply voltage in accordance with an expected variation with time of a DC impedance of said sensor element.

18. The method according to claim 15, wherein said controlling includes a first voltage application including applying a gas detection voltage between said first and second electrodes for detecting concentration of said specific gas component, and a second voltage application including applying said oxygen supply voltage between said first and second electrodes, said controlling including causing said second voltage application to apply said oxygen supply voltage between said first and second electrodes for a certain time period immediately after starting power supply to said electrical heater, and thereafter causing said first voltage application to apply said gas detection voltage between said first and second electrodes.

19. The method according to claim 18, wherein said second voltage application includes applying a predetermined constant voltage between said first and second electrodes as said oxygen supply voltage, said controlling includes applying a voltage intermediate between said oxygen supply voltage and said gas detection voltage during a transition period in which said second voltage application is switched to said first voltage application.

20. The method according to claim 13, wherein said controlling includes forcibly flowing a current from said first electrode to said second electrode to forcibly supply oxygen from the side of said second electrode to the side of said first electrode.

21. The gas sensor control apparatus according to claim 20, wherein said controlling includes passing a constant current in a direction from said first electrode to said second electrode to supply oxygen from the side of said second electrode to the side of said first electrode.

22. The method according to claim 13, wherein said controlling includes calculating an integration value of said sensor output integrated from a time when said gas sensor starts operation, said method further comprises stopping forced supplying of oxygen to the side of said first electrode when said integration value has reached a predetermined value.

23. The method according to claim 13, wherein said controlling includes calculating a value of integrated electric power supplied to an electrical heater of the gas sensor, said method further comprises stopping forced supplying of oxygen to the side of said first electrode when said integrated electric power has reached a predetermined value.

24. The method according to claim 13, wherein said gas sensor is mounted on an exhaust passage of an internal combustion engine, and said gas under measurement is an exhaust gas flowing through said exhaust passage.

* * * * *